(12) United States Patent
Sadelain et al.

(10) Patent No.: US 11,077,140 B2
(45) Date of Patent: Aug. 3, 2021

(54) CONSTITUTIVE EXPRESSION OF COSTIMULATORY LIGANDS ON ADOPTIVELY TRANSFERRED T LYMPHOCYTES

(71) Applicant: MEMORIAL SLOAN-KETTERING CANCER CENTER, New York, NY (US)

(72) Inventors: Michel Sadelain, New York, NY (US); Matthias Stephan, Boston, MA (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/135,678

(22) Filed: Sep. 19, 2018

(65) Prior Publication Data

US 2019/0000881 A1   Jan. 3, 2019

Related U.S. Application Data

(60) Division of application No. 14/734,969, filed on Jun. 9, 2015, now Pat. No. 10,117,897, which is a continuation of application No. 13/595,440, filed on Aug. 27, 2012, now Pat. No. 9,220,728, which is a division of application No. 12/593,751, filed as application No. PCT/US2008/004251 on Mar. 31, 2008, now Pat. No. 8,389,282.

(60) Provisional application No. 60/921,144, filed on Mar. 30, 2007.

(51) Int. Cl.
| | |
|---|---|
| *A61K 35/17* | (2015.01) |
| *A61K 39/00* | (2006.01) |
| *C12N 5/0783* | (2010.01) |
| *A61K 45/06* | (2006.01) |
| *C12N 15/85* | (2006.01) |
| *A61K 38/20* | (2006.01) |
| *C12N 7/00* | (2006.01) |
| *A61K 38/21* | (2006.01) |
| *A61K 35/12* | (2015.01) |

(52) U.S. Cl.
CPC .......... *A61K 35/17* (2013.01); *A61K 38/2013* (2013.01); *A61K 38/217* (2013.01); *A61K 39/0011* (2013.01); *A61K 45/06* (2013.01); *C12N 5/0636* (2013.01); *C12N 7/00* (2013.01); *C12N 15/85* (2013.01); *A61K 2035/122* (2013.01); *A61K 2035/124* (2013.01); *A61K 2039/5156* (2013.01); *A61K 2039/5158* (2013.01); *C12N 2501/25* (2013.01); *C12N 2501/51* (2013.01); *C12N 2501/599* (2013.01); *C12N 2510/00* (2013.01); *C12N 2799/04* (2013.01)

(58) Field of Classification Search
None
See application file for complete search history.

(56) References Cited

U.S. PATENT DOCUMENTS

| | | |
|---|---|---|
| 5,482,846 A | 1/1996 | Ingram et al. |
| 2003/0215427 A1 | 11/2003 | Jensen |
| 2005/0034179 A1 | 2/2005 | Sugamura et al. |
| 2011/0081327 A1 | 4/2011 | Nicolette et al. |

FOREIGN PATENT DOCUMENTS

| | | |
|---|---|---|
| WO | WO 2000/034494 A1 | 6/2000 |
| WO | PCT/US2008/004251 | 8/2008 |

OTHER PUBLICATIONS

EPO Form 1507S, Nov. 3, 2010, European Search Report for EP 07811186.1.
EPO Form 1507S, Mar. 22, 2010, Extended European Search Report for PCT/US08/04251.
U.S. Appl. No. 12/593,751 (U.S. Pat. No. 8,389,282), filed Mar. 8, 2010 (Mar. 5, 2013).
U.S. Appl. No. 13/595,440 (U.S. Pat. No. 9,220,728), filed Aug. 27, 2012 (Dec. 29, 2015).
U.S. Appl. No. 14/734,969 (U.S. Pat. No. 10,117,897), filed Jun. 9, 2015 (Nov. 6, 2018).
U.S. Appl. No. 12/593,751, Jan. 29, 2013, Issue Fee Payment.
U.S. Appl. No. 12/593,751, Dec. 13, 2012 Notice of Allowance.
U.S. Appl. No. 12/593,751, Nov. 28, 2012 Response to Non-Final Office Action.
U.S. Appl. No. 12/593,751, Sep. 5, 2012 Non-Final Office Action.
U.S. Appl. No. 12/593,751, Aug. 23, 2012 Amendment and Request for Continued Examination (RCE).
U.S. Appl. No. 12/593,751, Jul. 19, 2012 Issue Fee Payment.
U.S. Appl. No. 12/593,751, Apr. 19, 2012 Notice of Allowance.
U.S. Appl. No. 12/593,751, Mar. 12, 2012 Response to Non-Final Office Action.
U.S. Appl. No. 12/593,751, Oct. 11, 2011 Non-Final Office Action.
U.S. Appl. No. 12/593,751, Aug. 18, 2011 Response to Restriction Requirement.
U.S. Appl. No. 12/593,751, May 19, 2011 Restriction Requirement.
U.S. Appl. No. 13/595,440, Jun. 2, 2015 Issue Fee Payment.
U.S. Appl. No. 13/595,440 Mar. 3, 2015 Notice of Allowance.

(Continued)

*Primary Examiner* — Elly-Gerald Stoica
(74) *Attorney, Agent, or Firm* — Baker Botts L.L.P.

(57) ABSTRACT

The present invention provides immunoresponsive cells, including T cells, cytotoxic T cells, regulatory T cells, and Natural Killer (NK) cells, expressing at least one of an antigen-recognizing receptor and a co-stimulatory ligand and methods of use therefore for the treatment of neoplasia and other pathologies where an increase in an antigen-specific immune response is desired.

15 Claims, 31 Drawing Sheets

Specification includes a Sequence Listing.

(56) References Cited

OTHER PUBLICATIONS

U.S. Appl. No. 13/595,440, Feb. 4, 2015 Response to Non-Final Office Action.
U.S. Appl. No. 13/595,440, Nov. 5, 2014 Non-Final Office Action.
U.S. Appl. No. 13/595,440, Oct. 16, 2014 Response to Restriction Requirement.
U.S. Appl. No. 13/595,440, Aug. 20, 2014 Restriction Requirement Filed.
U.S. Appl. No. 13/595,440, Aug. 20, 2014 Applicant Initiated Interview Summary.
U.S. Appl. No. 13/595,440, Jun. 26, 2014, Restriction Requirement Filed.
U.S. Appl. No. 14/734,969, Sep. 27, 2018 Notice of Allowance.
U.S. Appl. No. 14/734,969, Sep. 20, 2018 Issue Fee Payment.
U.S. Appl. No. 14/734,969, Aug. 9, 2018 Notice of Allowance.
U.S. Appl. No. 14/734,969, Jun. 29, 2018 Notice of Allowance.
U.S. Appl. No. 14/734,969, Jun. 21, 2018 Notice of Allowance.
U.S. Appl. No. 14/734,969, Jun. 12, 2018 Response after Final Action.
U.S. Appl. No. 14/734,969, Apr. 17, 2018 Final Office Action.
U.S. Appl. No. 14/734,969, Feb. 28, 2018 Response to Non-Final Office Action.
U.S. Appl. No. 14/734,969, Nov. 28, 2017 Non-Final Office Action.
U.S. Appl. No. 14/734,969, Oct. 10, 2017 Response to Restriction Requirement.
U.S. Appl. No. 14/734,969, Aug. 16, 2017 Restriction Requirement.
U.S. Appl. No. 14/734,969, Jul. 3, 2017 Response to Restriction Requirement.
U.S. Appl. No. 14/734,969, May 12, 2017 Response to Restriction Requirement.
U.S. Appl. No. 14/734,969, Feb. 1, 2017 Restriction Requirement.
Baba et al, "Functional CD4 T cells after Intercellular Molecular Transfer of OX40 Ligand," The Journal of Immunology, 167:875-883 (2001).
Brentjens et al., "Eradication of systemic B-cell tumors by genetically targeted human T lymphocytes co-stimulated by CD80 and interleukin-15," Nature Medicine, Nature Publishing Group, New York, NY, US, 9(3):279-286 (2003).
Bukczynski et al., "Costimulatory ligand 4-1 BBL (CD137L) as an efficient adjuvant of human antiviral cytotoxic T cell responses," Proc. Natl. Acad. Sci. USA, 101:1291-1296 (2004).
Cannons et al., "4-1BB ligand induces cell division, sustains survival, and enhances effector function of CD4 and CD8 T cells with similar efficacy," J Immunol. 167(3):1313-1324 (Aug. 2001).
Cao et al., "Global Gene Expression Profiling in Interleukin-12-Induced Activation of CD8+ Cytotoxic T Lymphocytes against Mouse Mammary Carcinoma," Cell Mol. Immunol., 1(5):357-366 (2004).
Chai et al., "CD152 ligation by CDSO on T cells is required for the induction of unresponsiveness by costimulation-deficient antigen presentation," J Immunol. 165(6):3037-3042 (Sep. 2000).
Chouaib et al., "Interleukin 12 induces the differentiation of major histocompatibility complex class I-primed cytotoxic T-lymphocyte precursors into allospecific cytotoxic effectors," PNAS USA, 91:12659-12663 (1994).
Cooper et al., "Enhanced antilymphoma efficacy of CD 19-redirected influenza MP1-specific CTLs by cotransfer of T cells modified to present influenza MP1," Blood 105:1622-1631 (2005).
Extended European Search Report issued for corresponding European Application Serial No. 12179377.2, date of completion of the search Nov. 15, 2012, (10 pages).
Fallarino et al., "Antigen-specific regression of established tumors induced by active immunization with irradiated IL-12- but not B7-1-transfected tumor cells," International Immunology, 9(9):1259-1269 (1997).
Gade et al., "Targeted elimination of prostate cancer by genetically directed human T lymphocytes," Cancer Research, 65(19):9080-9088 (Oct. 2005).
Greenwald et al., "The B7 Family Revisited," Annu. Rev. Immunol. 23:515-548 (2005).
Grosenbach et al., "A recombinant vector expressing transgenes for four T-cell costimulatory molecules (0X40L, B7-1, ICAM-1, LFA-3) induces sustained CD4+ and CD8+ T-cell activation, protection from apoptosis, and enhanced cytokine production," Cellular Immunology, Academic Press, San Diego, CA, US, 222:45-57 (Mar. 1, 2003).
Guinn et al., "4-1BBL Cooperates with B7-1 and B7-2 in Converting a B Cell Lymphoma Cell Line into a Long-Lasting Antitumor Vaccine," The Journal of Immunology 162:5003-5010 (1999).
Heller et al., "Virus-specifi CD4 positive T cells: ready for direct attack," Jour. Exper. Med., 203(4):805-808 (Apr. 2006).
Heufler et al., "Interleukin-12 is produced by dendritic cells and mediates T helper 1 development as well as interferon-γ production by T helper 1 cells," Eur. J. Immunol. 26:659-668 (1996).
International Search Report dated Aug. 21, 2008 in International Application No. PCT/US08/04251.
Kowolik et al., "CD28 Costimulation Provided through a CD19-Specific Chimeric Antigen Receptor Enhances In vivo Persistence and Antitumor Efficacy of Adoptively Transferred T Cells," Cancer Research, 66(22):10995-11004 (2006).
Kowolik et al., "CD28-costimulation provided through a CD-19-specific chimeric immunoreceptor enhances in vivo persistence and anti-tumor efficacy of adoptively transferred T cells," Blood, vol. 106, No. 11, Part 1, Nov. 2005, p. 372A & 47th Annual Meeting of the American-Society-of-Hematology; Atlanta, GA; Dec. 10-13, 2005.
Martinez et al, "Biosynthetic burden and plasmid burden limit expression of chromosomally integrated heterologous genes (pdc, adhB) in *Escherichia coli*," Biotechnology Progress Sep. 17, 1999 American Chemical Society US, 15(5):891-897 (1999).
Maus et al., "Ex vivo expansion of polyclonal and antigen-specific cytotoxis T lymphocytes by artificial APCs expressing ligands for the T-cell receptor, CD28 and 4-1 BB," Nature Biotechnology, Nature Publishing Group, New York, NY, US, 20(2):143-148 (2002).
McFarland et al., "In Vitro Effects of IL-12 on HIV-1-Specific CTL Lines from HIV-1-Infected Children," The Journal of Immunology, 161:513-519 (1998).
Melero et al., "Amplification of Tumor Immunity by Gene Transfer of the Co-Stimulatory 4-1BB Ligand: Synergy with the CD28 Co-Stimulatory Pathway," European Journal of Immunology, Wiley-V C H Verlag GmbH & Co. KGAA, DE, 28(3):1116-1121 (1998).
Nelson, "IL-2, regulatory T cells, and tolerance," J. Immunology 172:3983-3988 (2004).
Paust et al., "Engagement of B7 on Effector T Cells by Regulatory T Cells Prevents Autoimmune Disease," PNAS 101(28):10398-10403 (Jul. 13, 2004).
Redmond et al., "The role of OX40-mediated co-stimulation in T cell activation and survival," Crit. Rev. Immunol. 29(3):187-201 (2009).
Sabzevari et al, "Acquisition of CD80 (B7-1) by T cells," The Journal of Immunology 166:2505-2513 (2001).
Sadelain et al., "Targeting Tumours with 1-15 Genetically Enhanced T Lymphocytes," Nature Reviews. Cancer, Nature Publishing Group, London GB, 3(1):35-45 (2003).
Serghides et al., "Evaluation of OX40 Ligand as a Costimulator of Human Antiviral Memory CD8 T Cell Responses: Comparison with B7.1 and 4-1BBL," The Journal of Immunology 175:6368-6377 (2005).
Stephan et al., "T cell-encoded CD80 and 4-1BBL induce auto- and transcostimulation, resulting in potent tumor rejection," Nature Medicine, 13(12):1440-1449 (2007).
Stockwin et al., "Dendritic cells: Immunological sentinels with a central role in health and disease," Immunol. Cell Biol. 78:91-102 (2000).
Taylor et al, "B7 Expression on T Cells Down-Regulates Immune Responses through CTLA-4 Ligation via R-T Interactions," The Journal of Immunology, 172:34-39 (2004).
Wang et al., "Effect of Tumor Vaccine of EL-4 Cell Transduced with IL-12 Gene in C57BL/6 Mice," Journal of Experimental Hematology, 8:118-121 (2000), with English abstract.

(56) References Cited

OTHER PUBLICATIONS

Yamada et al., "Retroviral expression of the human IL-2 gene in a murine T cell line results in cell growth autonomy and tumorigenicity," The EMBO Journal, 6(9):2705-2709 (1987).

Young et al., "In Vitro HIV-Specific CTL Activity from HIV-Seropositive Individuals Is Augmented by Interleukin-12 (IL-12)," AIDS Res Hum Retroviruses, 17:233-242 (2001).

Zheng et al., "Arming Tumor-Reactive T Cells with Costimulator B7-1 Enhances Therapeutic Efficacy of the T Cells," Cancer Research, 66(13):6793-6799 (2006).

Zhong et al., "Chimeric Antigen Receptors Combining 4-1 BB and CD28 Signaling Domains Augment P13kinase/AKT/Bc1-XL Activation and CD8+ T Cell-mediated Tumor Eradication," Molecular Therapy, 18(2):413-420 (2010).

Zhong et al., "Integrated CD28 and 4-1 BB Signals Strongly Potentiate CD8+ T Cell Mediated Eradication of Metastatic Prostate Cancer," Molecular Therapy, Academic Press, San Diego, CA, US, 13:S103 (Jan. 1, 2006).

Zufferey et al., "Multiply attenuated lentiviral vector achieves efficient gene delivery in vivo," Nature Biotechnology, 15:871-875 (1997).

Communication pursuant to Rule 114(2) EPC dated Aug. 12, 2019 for European Application No. 17206105.3: Third Party Observation (successful submission of observation took place on Jan. 8, 2019).

Kershaw, et al., "Supernatural T Cells: Genetic Modification of T Cells for Cancer Therapy," Nature Reviews, Immunology, vol. 5, pp. 928-940, Dec. 2005 (published online Nov. 18, 2005).

Liu, et al., "Transduction of an IL-2 Gene into Human Melanoma-Reactive Lymphocytes Results in Their Continued Growth in the Absence of Exogenous IL-2 and Maintenance of Specific Antitumor Activity," J. Immunol. Author Manuscript, 22 pages; published in final edited form as: J. Immunol., Dec. 1, 2001; 167(11), pp. 6356-6365.

Wagner, et al., "A strategy for treatment of Epstein-Barr virus-positive Hodgkin's disease by targeting interleukin 12 to the tumor environment using tumor antigen-specific T cells," Cancer Gene Therapy (2004) 11, pp. 81-91 (published online Dec. 19, 2003).

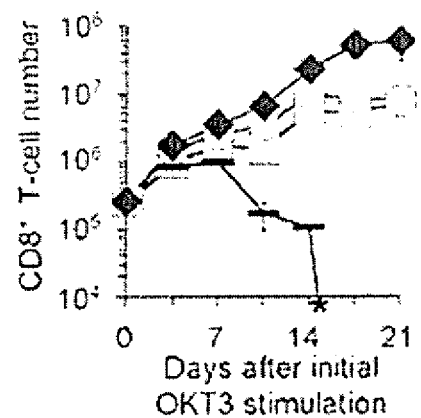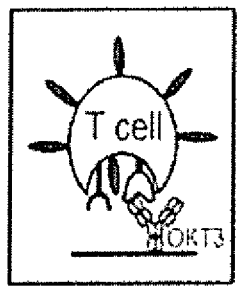
Figure 1b
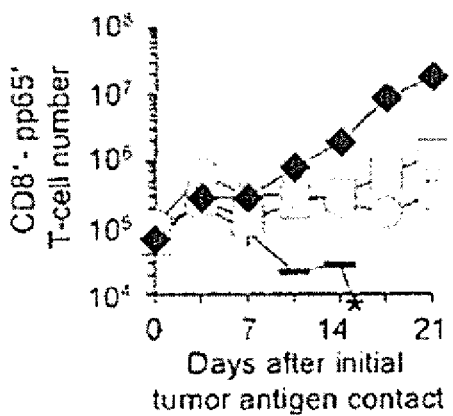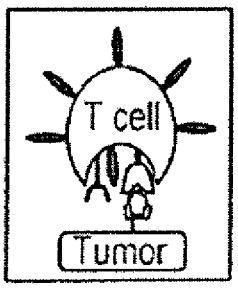
Figure 1d
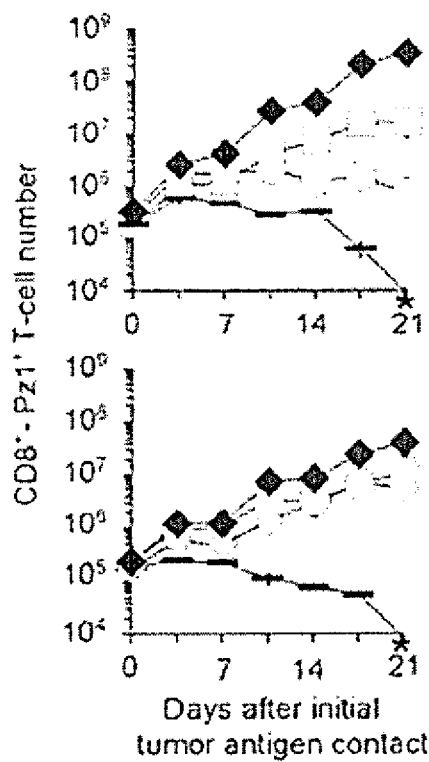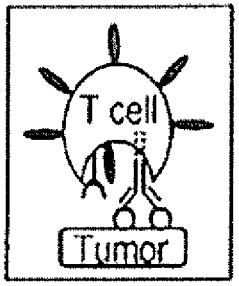
Figure 1f
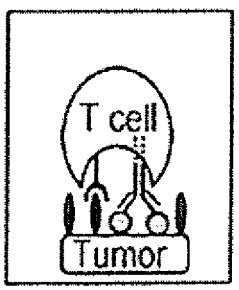

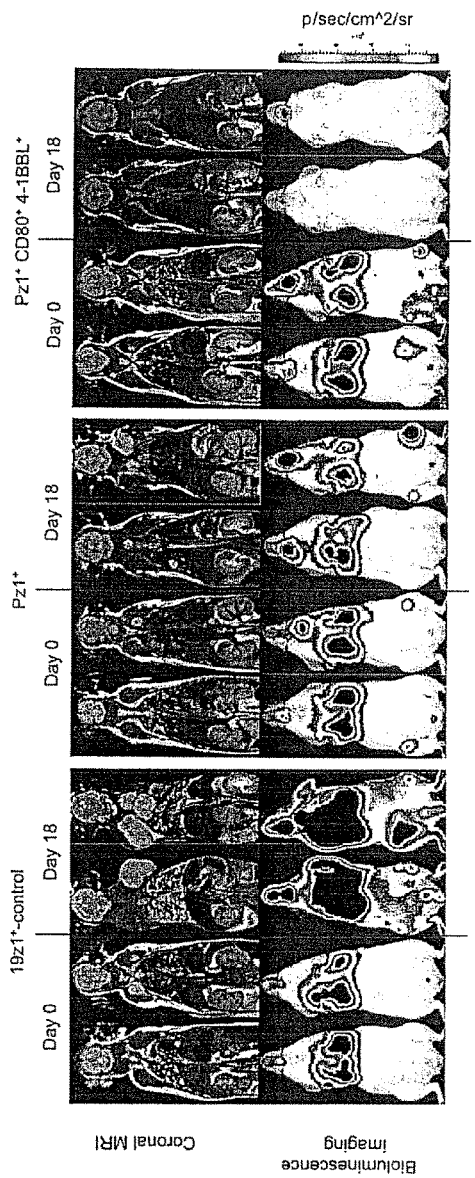
FIG. 2a
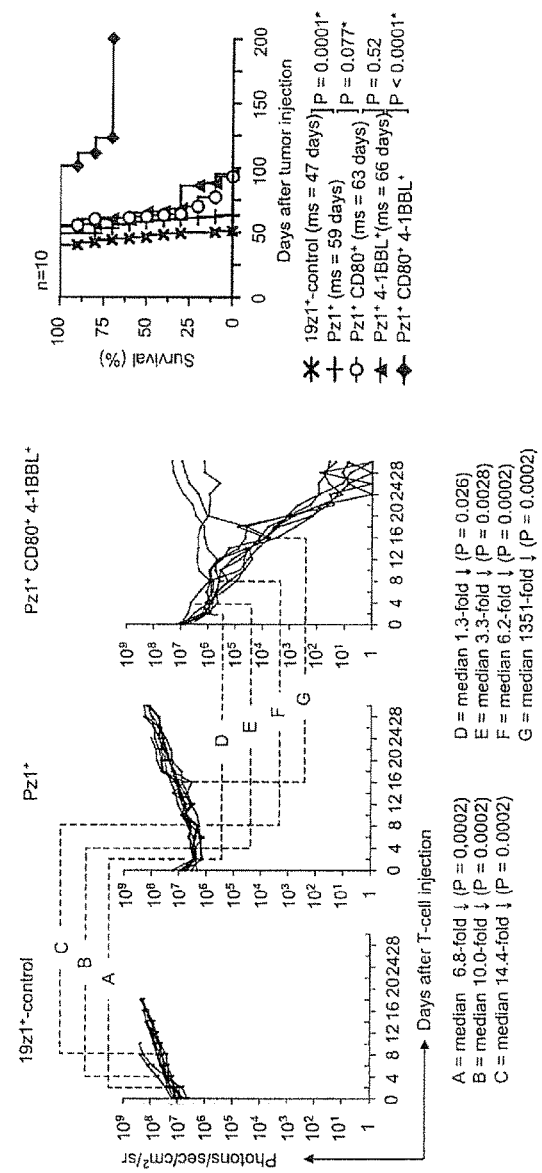
FIG. 2b
FIG. 2c

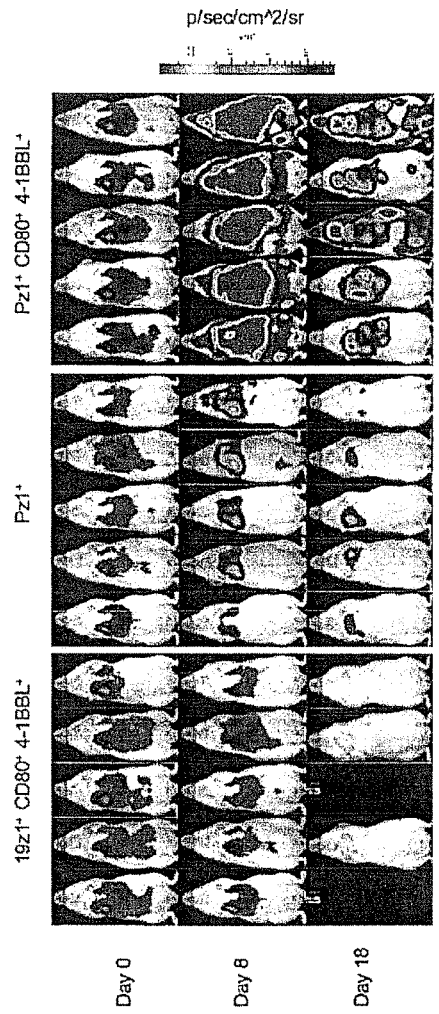
FIG. 3a
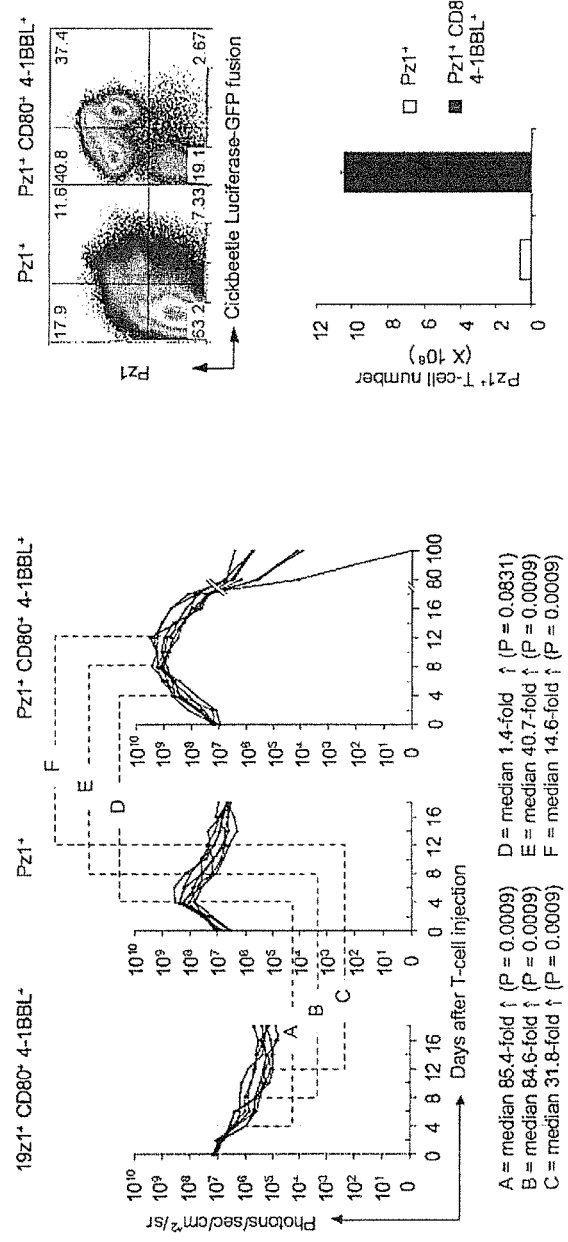
FIG. 3b
FIG. 3c
FIG. 3d

Figure 8 (cont'd)

```
                    recombinant soluble CD80 binds to CD28 and CD152 influencing T-cell
                    activation
     JOURNAL        Scand. J. Immunol. 66 (5), 529-537 (2007)
     PUBMED         17953528
     REMARK         GeneRIF: sCD80 in human serum adds a new member to the family of
                    soluble receptors, implying a network of soluble costimulatory
                    factors with functional relevance
  REFERENCE         5  (residues 1 to 288)
     AUTHORS        Dopheide,J.F., Sester,U., Schlitt,A., Horstick,G., Rupprecht,H.J.,
                    Munzel,T. and Blankenberg,S.
     TITLE          Monocyte-derived dendritic cells of patients with coronary artery
                    disease show an increased expression of costimulatory molecules
                    CD40, CD80 and CD86 in vitro
     JOURNAL        Coron. Artery Dis. 18 (7), 523-531 (2007)
     PUBMED         17925605
     REMARK         GeneRIF: CD40, CD80 and CD86 are upregulated in cultured
                    monocyte-derived dendritic cells of patients with coronary artery
                    disease
  REFERENCE         6  (residues 1 to 288)
     AUTHORS        Weiskirchen,R., Pino,J.D., Macalma,T., Bister,K. and Beckerle,M.C.
     TITLE          The cysteine-rich protein family of highly related LIM domain
                    proteins
     JOURNAL        J. Biol. Chem. 270 (48), 28946-28954 (1995)
     PUBMED         7499425
  REFERENCE         7  (residues 1 to 288)
     AUTHORS        Freeman,G.J., Disteche,C.M., Gribben,J.G., Adler,D.A.,
                    Freedman,A.S., Dougery,J. and Nadler,L.M.
     TITLE          The gene for B7, a costimulatory signal for T-cell activation, maps
                    to chromosomal region 3q13.3-3q21
     JOURNAL        Blood 79 (2), 489-494 (1992)
     PUBMED         1370389
  REFERENCE         8  (residues 1 to 288)
     AUTHORS        Selvakumar,A., Mohanraj,B.K., Eddy,R.L., Shows,T.B., White,P.C. and
                    Dupont,B.
     TITLE          Genomic organization and chromosomal location of the human gene
                    encoding the B-lymphocyte activation antigen B7
     JOURNAL        Immunogenetics 36 (3), 175-181 (1992)
     PUBMED         1377173
  REFERENCE         9  (residues 1 to 288)
     AUTHORS        Freeman,G.J., Gray,G.S., Gimmi,C.D., Lombard,D.B., Zhou,L.J.,
                    White,M., Fingeroth,J.D., Gribben,J.G. and Nadler,L.M.
     TITLE          Structure, expression, and T cell costimulatory activity of the
                    murine homologue of the human B lymphocyte activation antigen B7
     JOURNAL        J. Exp. Med. 174 (3), 625-631 (1991)
     PUBMED         1714935
  REFERENCE         10 (residues 1 to 288)
     AUTHORS        Freeman,G.J., Freedman,A.S., Segil,J.M., Lee,G., Whitman,J.F. and
                    Nadler,L.M.
     TITLE          B7, a new member of the Ig superfamily with unique expression on
                    activated and neoplastic B cells
     JOURNAL        J. Immunol. 143 (8), 2714-2722 (1989)
     PUBMED         2794510
  COMMENT           VALIDATED REFSEQ: This record has undergone validation or
                    preliminary review. The reference sequence was derived from
                    BP225173.1, BC042665.1 and AC073352.22.

Summary: The B-lymphocyte activation antigen B7-1 (formerly
                    referred to as B7) provides regulatory signals for T lymphocytes as
                    a consequence of binding to the CD28 (MIM 186760) and CTLA4 (MIM
                    123890) ligands of T cells.[supplied by OMIM].
```

Figure 8 (cont'd)

```
              Publication Note:  This RefSeq record includes a subset of the
              publications that are available for this gene. Please see the
              Entrez Gene record to access additional publications.
FEATURES             Location/Qualifiers
     source          1..288
                     /organism="Homo sapiens"
                     /db_xref="taxon:9606"
                     /chromosome="3"
                     /map="3q13.3-q21"
     Protein         1..288
                     /product="CD80 antigen precursor"
                     /note="costimulatory molecule variant IgV-CD80; CD80
                     antigen (CD28 antigen ligand 1, B7-1 antigen);
                     costimulatory factor CD80; B-lymphocyte activation antigen
                     B7"
     sig_peptide     1..34
                     /calculated_mol_wt=3754
     mat_peptide     35..288
                     /product="CD80 antigen"
                     /calculated_mol_wt=29312
     Region          37..139
                     /region_name="IG"
                     /note="Immunoglobulin; smart00409"
                     /db_xref="CDD:47718"
     Region          37..135
                     /region_name="V-set"
                     /note="Immunoglobulin V-set domain. This domain is found
                     in antibodies as well as neural protein P0 and CTL4
                     amongst others; pfam07686"
                     /db_xref="CDD:87333"
     Region          143..227
                     /region_name="C2-set_2"
                     /note="CD80-like C2-set immunoglobulin domain. These
                     domains belong to the immunoglobulin superfamily;
                     pfam08205"
                     /db_xref="CDD:71639"
     CDS             1..288
                     /gene="CD80"
                     /coded_by="NM_005191.3:396..1262"
                     /db_xref="CCDS:CCDS2989.1"
                     /db_xref="GeneID:941"
                     /db_xref="HGNC:1700"
                     /db_xref="HPRD:00202"
                     /db_xref="MIM:112203"
ORIGIN
        1 mghtrrqgts pskcpylnff qllvlaglsh fcsgvihvtk evkevatlsc ghnvsveela
       61 qtriywqkek kmvltmmsgd mniwpeyknr tifditnnls ivilalrpsd egtyecvvlk
      121 yekdafkreh laevtlsvka dfptpsisdf eiptsnirri icstsggfpe phlswlenge
      181 elnainttvs qdpetelyav ssskldfnmtt nhsfmcliky ghlrvnqtfn wnttkqehfp
      241 dnllpswait lisvngifvi ccltycfapr crerrrnerl rresvrpv
//
```

Figure 8 (cont'd)

```
                Shapiro,N., Bhat,N.K., Hopkins,R.F., Hsie,F., Driscoll,T.,
                Soares,M.B., Casavant,T.L., Scheetz,T.E., Brown-stein,M.J.,
                Usdin,T.B., Toshiyuki,S., Carninci,P., Piao,Y., Dudekula,D.B.,
                Ko,M.S., Kawakami,K., Suzuki,Y., Sugano,S., Gruber,C.E.,
                Smith,M.R., Simmons,B., Moore,T., Waterman,R., Johnson,S.L.,
                Ruan,Y., Wei,C.L., Mathavan,S., Gunaratne,P.H., Wu,J., Garcia,A.M.,
                Hulyk,S.W., Fuh,E., Yuan,Y., Sneed,A., Kowis,C., Hodgson,A.,
                Muzny,D.M., McPherson,J., Gibbs,R.A., Fahey,J., Helton,E.,
                Ketteman,M., Madan,A., Rodrigues,S., Sanchez,A., Whiting,M.,
                Madari,A., Young,A.C., Wetherby,K.D., Granite,S.J., Kwong,P.N.,
                Brinkley,C.P., Pearson,R.L., Bouffard,G.G., Blakesly,R.W.,
                Green,E.D., Dickson,M.C., Rodriguez,A.C., Grimwood,J., Schmutz,J.,
                Myers,R.M., Butterfield,Y.S., Griffith,M., Griffith,O.L.,
                Krzywinski,M.I., Liao,N., Morin,R., Palmquist,D., Petrescu,A.S.,
                Skalska,U., Smailus,D.E., Stott,J.M., Schnerch,A., Schein,J.E.,
                Jones,S.J., Holt,R.A., Baross,A., Marra,M.A., Clifton,S.,
                Makowski,K.A., Bosak,S. and Malek,J.
  CONSRTM       MGC Project Team
  TITLE         The status, quality, and expansion of the NIH full-length cDNA
                project: the Mammalian Gene Collection (MGC)
  JOURNAL       Genome Res  14 (10B), 2121-2127 (2004)
   PUBMED       15489334
  REMARK        NUCLEOTIDE SEQUENCE [LARGE SCALE MRNA].
                TISSUE=Lung
                Erratum:[Genome Res. 2006 Jun;16(6):804. Morrin, Ryan [corrected to
                Morin, Ryan]]
  COMMENT       On or before Feb 16, 2007 this sequence version replaced
                gi:121941506, gi:7512264.
                [FUNCTION] Cytokine that binds to TNFRSF9. Induces the
                proliferation of activated peripheral blood T-cells. May have a
                role in activation-induced cell death (AICD). May play a role in
                cognate interactions between T-cells and B-cells/macrophages.
                [SUBUNIT] Homotrimer (Potential).
                [SUBCELLULAR LOCATION] Membrane; Single-pass type II membrane
                protein.
                [TISSUE SPECIFICITY] Expressed in brain, placenta, lung, skeletal
                muscle and kidney.
                [SIMILARITY] Belongs to the tumor necrosis factor family.
  FEATURES             Location/Qualifiers
       source          1..254
                       /organism="Homo sapiens"
                       /db_xref="taxon:9606"
       gene            1..254
                       /gene="TNFSF9"
       Protein         1..254
                       /gene="TNFSF9"
                       /product="Tumor necrosis factor ligand superfamily member
                       9"
       Region          1..254
                       /gene="TNFSF9"
                       /region_name="Mature chain"
                       /experiment="experimental evidence, no additional details
                       recorded"
                       /note="Tumor necrosis factor ligand superfamily member 9.
                       /FTId=PRO_0000185501."
       Region          1..28
                       /gene="TNFSF9"
                       /region_name="Topological domain"
                       /inference="non-experimental evidence, no additional
                       details recorded"
```

Figure 8 (cont'd)

```
                         /note="Cytoplasmic (Potential)."
     Region              17
                         /gene="TNFSF9"
                         /region_name="Variant"
                         /experiment="experimental evidence, no additional details
                         recorded"
                         /note="P -> A (in dbSNP:rs442511). /FTId=VAR_011928."
     Region              29..49
                         /gene="TNFSF9"
                         /region_name="Transmembrane region"
                         /inference="non-experimental evidence, no additional
                         details recorded"
                         /note="Signal-anchor for type II membrane protein
                         (Potential)."
     Region              35..41
                         /gene="TNFSF9"
                         /region_name="Compositionally biased region"
                         /experiment="experimental evidence, no additional details
                         recorded"
                         /note="Poly-Leu."
     Region              50..254
                         /gene="TNFSF9"
                         /region_name="Topological domain"
                         /inference="non-experimental evidence, no additional
                         details recorded"
                         /note="Extracellular (Potential)."
     Region              91..238
                         /gene="TNFSF9"
                         /region_name="TNF"
                         /note="Tumor Necrosis Factor; TNF superfamily members
                         include the cytokines: TNF (TNF-alpha), LT
                         (lymphotoxin-alpha, TNF-beta), CD40 ligand, Apo2L (TRAIL),
                         Fas ligand, and osteoprotegerin (OPG) ligand; cd00184"
                         /db_xref="CDD:29146"
     Site                order(94,142,144,199,204,234,238)
                         /gene="TNFSF9"
                         /site_type="other"
                         /note="trimer interface"
                         /db_xref="CDD:29146"
     Site                order(110..111,116,162,169,176)
                         /gene="TNFSF9"
                         /site_type="other"
                         /note="receptor binding sites"
                         /db_xref="CDD:29146"
ORIGIN
        1 meyasdasld peapwppapr aracrvlpwa lvaglllll laaacavfla cpwavsgara
       61 spgsaasprl regpelspdd paglldlrqg mfaqlvaqnv llidgplswy sdpglagvsl
      121 tgglsykedt kelvvakagv yyvffqlelr rvvagegsgs vslalhlqpl rsaagaaala
      181 ltvdlppass earnsafgfq grllhlsagq rlgvhlhtea rarhawqltq gatvlglfrv
      241 tpeipaglps prse
//
```

Figure 8 (cont'd)

NCBI Protein [Sign In] [Regis...] My N(

PubMed  Nucleotide  Protein  Genome  Structure  PMC  Taxonomy  OMIM  Book:

Search Protein _____ for _____ [Go] [Clear]

Limits    Preview/Index    History    Clipboard    Details

Display GenPept    Show 5    Send to

Range: from begin    to end    Features: [+] [Refresh]

☐ 1: BAB18304. Reports OX40 ligand [Homo...[gi:11275538]    BLink, Links

Features  Sequence

```
LOCUS       BAB18304                  67 aa          linear   PRI 19-OCT-2004
DEFINITION  OX40 ligand [Homo sapiens].
ACCESSION   BAB18304
VERSION     BAB18304.1  GI:11275538
DBSOURCE    accession AB042988.2
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1
  AUTHORS   Hikami,K., Tsuchiya,N. and Tokunaga,K.
  TITLE     New variations in human OX40 ligand (CD134L) gene
  JOURNAL   Genes Immun. 1 (8), 521-522 (2000)
   PUBMED   11197696
REFERENCE   2  (residues 1 to 67)
  AUTHORS   Hikami,K., Tsuchiya,N. and Tokunaga,K.
  TITLE     Direct Submission
  JOURNAL   Submitted (19-MAY-2000) Koki Hikami, University of Tokyo,
            Department of Human Genetics; 7-3-1 Hongo, Bunkyo-ku, Tokyo
            113-0033, Japan (E-mail:kokihikami@mail.goo.ne.jp,
            Tel:81-3-5841-3693, Fax:81-3-5802-8619)
FEATURES             Location/Qualifiers
     source          1..67
                     /organism="Homo sapiens"
                     /db_xref="taxon:9606"
                     /chromosome="1"
                     /map="1q25"
     Protein         1..67
                     /product="OX40 ligand"
     CDS             1..67
                     /gene="OX40L"
                     /coded_by="join(AB042988.2:55..207,AB042988.2:462..>510)"
ORIGIN
        1 mervqpleen vgnaarprfe mklllvasv iqglglllcf tyiclhfsal qvshrypriq
       61 sikvqft
//
```

Disclaimer | Write to the Help Desk
NCBI | NLM | NIH

Figure 8 (cont'd)

NCBI Protein [Sign In] [Regis

PubMed  Nucleotide  Protein  Genome  Structure  PMC  Taxonomy  OMIM  Book:

Search | Protein | for [_____] [Go] [Clear]

Limits   Preview/Index   History   Clipboard   Details

Display GenPept  Show 5  Send to

Range: from |begin  to |end  Features: ☑CDD [+] [Refresh]

☐ 1: NP_001243. Reports tumor necrosis fa...[gi:4507605]          BLink, Conserved
                                                                  Domains, Links Comment   Features   Sequence

```
LOCUS       NP_001243                193 aa            linear   PRI 11-FEB-2008
DEFINITION  tumor necrosis factor ligand superfamily, member 7 [Homo sapiens].
ACCESSION   NP_001243
VERSION     NP_001243.1  GI:4507605
DBSOURCE    REFSEQ: accession NM_001252.3
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (residues 1 to 193)
  AUTHORS   Yang,Z.Z., Novak,A.J., Ziesmer,S.C., Witzig,T.E. and Ansell,S.M.
  TITLE     CD70+ non-Hodgkin lymphoma B cells induce Foxp3 expression and
            regulatory function in intratumoral CD4+CD25 T cells
  JOURNAL   Blood 110 (7), 2537-2544 (2007)
   PUBMED   17615291
  REMARK    GeneRIF: reveal a novel role for non-Hodgkin lymphoma B cells in
            the development of intratumoral regulatory T cells
REFERENCE   2  (residues 1 to 193)
  AUTHORS   van Oosterwijk,M.F., Juwana,H., Arens,R., Tesselaar,K., van
            Oers,M.H., Eldering,E. and van Lier,R.A.
  TITLE     CD27-CD70 interactions sensitise naive CD4+ T cells for
            IL-12-induced Th1 cell development
  JOURNAL   Int. Immunol. 19 (6), 713-718 (2007)
   PUBMED   17548342
  REMARK    GeneRIF: CD27-CD70 interactions may promote Th1 cell formation by
            permitting naive T cells to respond to differentiation signals and
            by promoting survival of activated effector T cells.
REFERENCE   3  (residues 1 to 193)
  AUTHORS   Diegmann,J., Junker,K., Loncarevic,I.F., Michel,S., Schimmel,B. and
            von Eggeling,F.
  TITLE     Immune escape for renal cell carcinoma: CD70 mediates apoptosis in
            lymphocytes
  JOURNAL   Neoplasia 8 (11), 933-938 (2006)
   PUBMED   17132225
  REMARK    GeneRIF: Apoptosis mediated by exposure to the CD70 secreted by
            tumor cells may contribute to the failure of renal cell carcinoma
            patients to develop an effective lymphocyte-mediated antitumor
            response
REFERENCE   4  (residues 1 to 193)
  AUTHORS   Adam,P.J., Terrett,J.A., Steers,G., Stockwin,L., Loader,J.A.,
```

Figure 8 (cont'd)

|  |  |
|---|---|
|  | Fletcher,G.C., Lu,L.S., Leach,B.I., Mason,S., Stamps,A.C., Boyd,R.S., Pezzella,F., Gatter,K.C. and Harris,A.L. |
| TITLE | CD70 (TNFSF7) is expressed at high prevalence in renal cell carcinomas and is rapidly internalised on antibody binding |
| JOURNAL | Br. J. Cancer 95 (3), 298-306 (2006) |
| PUBMED | 16892042 |
| REMARK | GeneRIF: Immunocytochemical analysis demonstrated that binding of an anti-CD70 antibody to CD70(TNFSF7), endogenously expressed on the surface of A498 and 786-O cell lines resulted in the rapid internalisation of the antibody-receptor complex. |
| REFERENCE | 5 (residues 1 to 193) |
| AUTHORS | Huang,J., Kerstann,K.W., Ahmadzadeh,M., Li,Y.F., El-Gamil,M., Rosenberg,S.A. and Robbins,P.F. |
| TITLE | Modulation by IL-2 of CD70 and CD27 expression on CD8+ T cells: importance for the therapeutic effectiveness of cell transfer immunotherapy |
| JOURNAL | J. Immunol. 176 (12), 7726-7735 (2006) |
| PUBMED | 16751420 |
| REMARK | GeneRIF: Interaction of CD70 with CD27 plays a direct role in T cell activation mediated by IL-2. |
| REFERENCE | 6 (residues 1 to 193) |
| AUTHORS | Kobata,T., Jacquot,S., Kozlowski,S., Agematsu,K., Schlossman,S.F. and Morimoto,C. |
| TITLE | CD27-CD70 interactions regulate B-cell activation by T cells |
| JOURNAL | Proc. Natl. Acad. Sci. U.S.A. 92 (24), 11249-11253 (1995) |
| PUBMED | 7479974 |
| REFERENCE | 7 (residues 1 to 193) |
| AUTHORS | Brown,G.R., Meek,K., Nishioka,Y. and Thiele,D.L. |
| TITLE | CD27-CD27 ligand/CD70 interactions enhance alloantigen-induced proliferation and cytolytic activity in CD8+ T lymphocytes |
| JOURNAL | J. Immunol. 154 (8), 3686-3695 (1995) |
| PUBMED | 7706711 |
| REFERENCE | 8 (residues 1 to 193) |
| AUTHORS | Hintzen,R.Q., Lens,S.M., Koopman,G., Pals,S.T., Spits,H. and van Lier,R.A. |
| TITLE | CD70 represents the human ligand for CD27 |
| JOURNAL | Int. Immunol. 6 (3), 477-480 (1994) |
| PUBMED | 8186199 |
| REFERENCE | 9 (residues 1 to 193) |
| AUTHORS | Hintzen,R.Q., Lens,S.M., Beckmann,M.P., Goodwin,R.G., Lynch,D. and van Lier,R.A. |
| TITLE | Characterization of the human CD27 ligand, a novel member of the TNF gene family |
| JOURNAL | J. Immunol. 152 (4), 1762-1773 (1994) |
| PUBMED | 8120385 |
| REFERENCE | 10 (residues 1 to 193) |
| AUTHORS | Bowman,M.R., Crimmins,M.A., Yetz-Aldape,J., Kriz,R., Kelleher,K. and Herrmann,S. |
| TITLE | The cloning of CD70 and its identification as the ligand for CD27 |
| JOURNAL | J. Immunol. 152 (4), 1756-1761 (1994) |
| PUBMED | 8120384 |
| COMMENT | REVIEWED REFSEQ: This record has been curated by NCBI staff. The reference sequence was derived from AC008760.7. |
|  | Summary: The protein encoded by this gene is a cytokine that belongs to the tumor necrosis factor (TNF) ligand family. This cytokine is a ligand for TNFRSF27/CD27. It is a surface antigen on activated, but not on resting, T and B lymphocytes. It induces proliferation of costimulated T cells, enhances the generation of cytolytic T cells, and contributes to T cell activation. This |

Figure 8 (cont'd)

cytokine is also reported to play a role in regulating B-cell activation, cytotoxic function of natural killer cells, and immunoglobulin sythesis.

Publication Note: This RefSeq record includes a subset of the publications that are available for this gene. Please see the Entrez Gene record to access additional publications.

```
FEATURES             Location/Qualifiers
     source          1..193
                     /organism="Homo sapiens"
                     /db_xref="taxon:9606"
                     /chromosome="19"
                     /map="19p13"
     Protein         1..193
                     /product="tumor necrosis factor ligand superfamily, member
                     7"
                     /note="CD70 antigen; CD27 ligand; surface antigen CD70;
                     Ki-24 antigen; tumor necrosis factor (ligand) superfamily,
                     member 7"
                     /calculated_mol_wt=20987
     Region          58..189
                     /region_name="TNF"
                     /note="Tumor Necrosis Factor; TNF superfamily members
                     include the cytokines: TNF (TNF-alpha), LT
                     (lymphotoxin-alpha, TNF-beta), CD40 ligand, Apo2L (TRAIL),
                     Fas ligand, and osteoprotegerin (OPG) ligand; cd00184"
                     /db_xref="CDD:29146"
     Site            order(61,105,107,154,159,185,189)
                     /site_type="other"
                     /note="trimer interface"
                     /db_xref="CDD:29146"
     Site            order(76..77,84,119,126,129)
                     /site_type="other"
                     /note="receptor binding sites"
                     /db_xref="CDD:29146"
     CDS             1..193
                     /gene="CD70"
                     /coded_by="NM_001252.3:151..732"
                     /db_xref="CCDS:CCDS12170.1"
                     /db_xref="GeneID:970"
                     /db_xref="HGNC:11937"
                     /db_xref="HPRD:18515"
                     /db_xref="MIM:602840"
ORIGIN
        1 mpeegsgcsv rrrpygcvlr aalvplvagl viclvvciqr faqaqqqlpl eslgwdvael
       61 qlnhtgpqqd prlywqggpa lgrsflhgpe ldkgqlrihr dgiymvhiqv tlaicsstta
      121 srhhpttlav gicspasrsi sllrlsfhqg ctiasqrltp largdtlctn ltgtllpsrn
      181 tdetffgvqw vrp
//
```

Disclaimer | Write to the Help Desk
NCBI | NLM | NIH

Figure 8 (cont'd)

NCBI Protein [Sign In] [Regis

PubMed　　Nucleotide　　Protein　　Genome　　Structure　　PMC　　Taxonomy　　OMIM　　Books

Search Protein ▧ for _____ [Go] [Clear]

Limits　　　Preview/Index　　History　　Clipboard　　Details

Display GenPept ▧ Show 5 ▧ Send to ▧

Range: from |begin     to |end     Features: ☐ SNP ☑ CDD [+] [Refresh]

☐ 1: <u>NP_742011</u>. Reports tumor necrosis fa...[gi:25952147]　　　　BLink, Conserved Domains, Links <u>Comment</u>　<u>Features</u>　<u>Sequence</u>

```
LOCUS       NP_742011                204 aa            linear   PRI 16-MAR-2008
DEFINITION  tumor necrosis factor ligand superfamily, member 14 isoform 2 [Homo
            sapiens].
ACCESSION   NP_742011
VERSION     NP_742011.1  GI:25952147
DBSOURCE    REFSEQ: accession NM_172014.1
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (residues 1 to 204)
  AUTHORS   Pawlak,K., Pawlak,D. and Mysliwiec,M.
  TITLE     LIGHT--a new member of the TNF superfamily in the plasma, dialysate
            and urine of uremic patients; the impact of residual diuresis and
            presence of viral hepatitis
  JOURNAL   Clin. Biochem. 40 (16-17), 1240-1244 (2007)
   PUBMED   17826757
  REMARK    GeneRIF: The plasma levels of LIGHT seem to be similar in
            hemodialysis (HD) patients and healthy subjects and were not
            affected by gender, age, the mean period of HD history, disease
            etiology, type of medication and type of using dialysis membrane.
REFERENCE   2  (residues 1 to 204)
  AUTHORS   Celik,S., Langer,H., Stellos,K., May,A.E., Shankar,V., Kurz,K.,
            Katus,H.A., Gawaz,M.P. and Dengler,T.J.
  TITLE     Platelet-associated LIGHT (TNFSF14) mediates adhesion of platelets
            to human vascular endothelium
  JOURNAL   Thromb. Haemost. 98 (4), 798-805 (2007)
   PUBMED   17938804
  REMARK    GeneRIF: platelet-associated LIGHT is involved in adhesion of
            platelets to endothelium while soluble LIGHT induces a
            pro-inflammatory state in vascular endothelial cells
REFERENCE   3  (residues 1 to 204)
  AUTHORS   Loeffler,M., Le'Negrate,G., Krajewska,M. and Reed,J.C.
  TITLE     Attenuated Salmonella engineered to produce human cytokine LIGHT
            inhibit tumor growth
  JOURNAL   Proc. Natl. Acad. Sci. U.S.A. 104 (31), 12879-12883 (2007)
   PUBMED   17652173
  REMARK    GeneRIF: attenuated Salmonella typhimurium expressing LIGHT
            inhibited growth of primary tumors, as well as the dissemination of
            pulmonary metastases, in various mouse tumor models employing
```

Figure 8 (cont'd)

```
                    murine carcinoma cell lines in immunocompetent mice
REFERENCE   4  (residues 1 to 204)
  AUTHORS   Nadiminty,N., Chun,J.Y., Hu,Y., Dutt,S., Lin,X. and Gao,A.C.
  TITLE     LIGHT, a member of the TNF superfamily, activates Stat3 mediated by
            NIK pathway
  JOURNAL   Biochem. Biophys. Res. Commun. 359 (2), 379-384 (2007)
   PUBMED   17543278
  REMARK    GeneRIF: in addition to activating NF-kappaB/p52, LIGHT also
            activates Stat3 through the NIK pathway
REFERENCE   5  (residues 1 to 204)
  AUTHORS   Gill,R.M., Coleman,N.M. and Hunt,J.S.
  TITLE     Differential cellular expression of LIGHT and its receptors in
            early gestation human placentas
  JOURNAL   J. Reprod. Immunol. 74 (1-2), 1-6 (2007)
   PUBMED   17010447
  REMARK    GeneRIF: LIGHT system may regulate early to middle stages of
            placental development via cell-specific, temporally programmed
            expression of the ligand and its receptors, and may also assist in
            preserving placental immune privilege.
REFERENCE   6  (residues 1 to 204)
  AUTHORS   Yu,K.Y., Kwon,B., Ni,J., Zhai,Y., Ebner,R. and Kwon,B.S.
  TITLE     A newly identified member of tumor necrosis factor receptor
            superfamily (TR6) suppresses LIGHT-mediated apoptosis
  JOURNAL   J. Biol. Chem. 274 (20), 13733-13736 (1999)
   PUBMED   10318773
REFERENCE   7  (residues 1 to 204)
  AUTHORS   Harrop,J.A., McDonnell,P.C., Brigham-Burke,M., Lyn,S.D., Minton,J.,
            Tan,K.B., Dede,K., Spampanato,J., Silverman,C., Hensley,P.,
            DiPrinzio,R., Emery,J.G., Deen,K., Eichman,C., Chabot-Fletcher,M.,
            Truneh,A. and Young,P.R.
  TITLE     Herpesvirus entry mediator ligand (HVEM-L), a novel ligand for
            HVEM/TR2, stimulates proliferation of T cells and inhibits HT29
            cell growth
  JOURNAL   J. Biol. Chem. 273 (42), 27548-27556 (1998)
   PUBMED   9765287
REFERENCE   8  (residues 1 to 204)
  AUTHORS   Zhai,Y., Guo,R., Hsu,T.L., Yu,G.L., Ni,J., Kwon,B.S., Jiang,G.W.,
            Lu,J., Tan,J., Ugustus,M., Carter,K., Rojas,L., Zhu,F., Lincoln,C.,
            Endress,G., Xing,L., Wang,S., Oh,K.O., Gentz,R., Ruben,S.,
            Lippman,M.E., Hsieh,S.L. and Yang,D.
  TITLE     LIGHT, a novel ligand for lymphotoxin beta receptor and TR2/HVEM
            induces apoptosis and suppresses in vivo tumor formation via gene
            transfer
  JOURNAL   J. Clin. Invest. 102 (6), 1142-1151 (1998)
   PUBMED   9739048
REFERENCE   9  (residues 1 to 204)
  AUTHORS   Marsters,S.A., Sheridan,J.P., Pitti,R.M., Brush,J., Goddard,A. and
            Ashkenazi,A.
  TITLE     Identification of a ligand for the death-domain-containing receptor
            Apo3
  JOURNAL   Curr. Biol. 8 (9), 525-528 (1998)
   PUBMED   9560343
REFERENCE   10 (residues 1 to 204)
  AUTHORS   Mauri,D.N., Ebner,R., Montgomery,R.I., Kochel,K.D., Cheung,T.C.,
            Yu,G.L., Ruben,S., Murphy,M., Eisenberg,R.J., Cohen,G.H.,
            Spear,P.G. and Ware,C.F.
  TITLE     LIGHT, a new member of the TNF superfamily, and lymphotoxin alpha
            are ligands for herpesvirus entry mediator
  JOURNAL   Immunity 8 (1), 21-30 (1998)
   PUBMED   9462508
```

Figure 8 (cont'd)

```
COMMENT     REVIEWED REFSEQ: This record has been curated by NCBI staff. The
            reference sequence was derived from AY028261.1 and AF064090.1.

Summary: The protein encoded by this gene is a member of the tumor
            necrosis factor (TNF) ligand family. This protein is a ligand for
            TNFRSF14, which is a member of the tumor necrosis factor receptor
            superfamily, and which is also known as a herpesvirus entry
            mediator (HVEM). This protein may function as a costimulatory
            factor for the activation of lymphoid cells and as a deterrent to
            infection by herpesvirus. This protein has been shown to stimulate
            the proliferation of T cells, and trigger apoptosis of various
            tumor cells. This protein is also reported to prevent tumor
            necrosis factor alpha mediated apoptosis in primary hepatocyte. Two
            alternatively spliced transcript variant encoding distinct isoforms
            have been reported.

Transcript Variant: This variant (2) lacks an in-frame coding
            segment compared to variant 1, resulting an isoform (2) that lacks
            an internal region, as compared to isoform 1.

Publication Note: This RefSeq record includes a subset of the
            publications that are available for this gene. Please see the
            Entrez Gene record to access additional publications.
FEATURES             Location/Qualifiers
     source          1..204
                     /organism="Homo sapiens"
                     /db_xref="taxon:9606"
                     /chromosome="19"
                     /map="19p13.3"
     Protein         1..204
                     /product="tumor necrosis factor ligand superfamily, member
                     14 isoform 2"
                     /note="delta transmembrane LIGHT; tumor necrosis factor
                     superfamily member LIGHT; herpesvirus entry mediator A;
                     tumor necrosis factor receptor-like 2; ligand for
                     herpesvirus entry mediator"
                     /calculated_mol_wt=22265
     Region          58..202
                     /region_name="TNF"
                     /note="Tumor Necrosis Factor; TNF superfamily members
                     include the cytokines: TNF (TNF-alpha), LT
                     (lymphotoxin-alpha, TNF-beta), CD40 ligand, Apo2L (TRAIL),
                     Fas ligand, and osteoprotegerin (OPG) ligand; cd00184"
                     /db_xref="CDD:29146"
     Site            order(61,106,108,166,171,198,202)
                     /site_type="other"
                     /note="trimer interface"
                     /db_xref="CDD:29146"
     Site            order(79..80,85,127,134,139)
                     /site_type="other"
                     /note="receptor binding sites"
                     /db_xref="CDD:29146"
     CDS             1..204
                     /gene="TNFSF14"
                     /coded_by="NM_172014.1:383..997"
                     /note="isoform 2 is encoded by transcript variant 2"
                     /db_xref="GeneID:8740"
                     /db_xref="HGNC:11930"
                     /db_xref="MIM:604520"
ORIGIN
```

Figure 8 (cont'd)

```
  1 meesvvrpsv fvvdgqtdip ftrlgrshrr qscsvardgp agsweqliqe rrshevnpaa
 61 hltgansslt gsggpllwet qlglaflrgl syhdgalvvt kagyyyiysk vqlggvgcpl
121 glastithgl ykrtprypee lellvsqqsp cgratsssrv wwdssflggv vhleageevv
181 vrvlderlvr lrdgtrsyfg afmv
//
```

Disclaimer | Write to the Help Desk
NCBI | NLM | NIH

Figure 8 (cont'd)

```
                                                                    My N(
  NCBI                                    Protein  [Sign In] [Regis
 PubMed     Nucleotide    Protein    Genome    Structure    PMC    Taxonomy    OMIM    Books
Search Protein           ▓ for                                        Go  Clear
            Limits       Preview/Index    History     Clipboard      Details
Display GenPept          ▓ Show 5    ▓ Send to ▓
Range: from  begin       to  end          Features:  ☑ CDD [+]  Refresh
```

☐ 1: AAB97877. Reports CD30L protein [Ho...[gi:2815515]          BLink, Conserved
                                                                  Domains, Links Features  Sequence

```
LOCUS       AAB97877                 234 aa            linear   PRI 28-JAN-1998
DEFINITION  CD30L protein [Homo sapiens].
ACCESSION   AAB97877
VERSION     AAB97877.1  GI:2815515
DBSOURCE    locus HSCD30L1 accession AF006381.1
            locus HSCD30L2 accession AF006382.1
            locus HSCD30L3 accession AF006383.1
            locus HSCD30L4 accession AF006384.1
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (residues 1 to 234)
  AUTHORS   Croager,E.J. and Abraham,L.J.
  TITLE     Characterisation of the human CD30 ligand gene structure
  JOURNAL   Biochim. Biophys. Acta 1353 (3), 231-235 (1997)
  PUBMED    9349718
REFERENCE   2  (residues 1 to 234)
  AUTHORS   Croager,E.J. and Abraham,L.J.
  TITLE     Direct Submission
  JOURNAL   Submitted (02-JUN-1997) Biochemistry, University of Western
            Australia, Entrance 2, Hackett Drive, Nedlands, Western Australia
            6907, Australia
COMMENT     Method: conceptual translation.
FEATURES             Location/Qualifiers
     source          1..234
                     /organism="Homo sapiens"
                     /db_xref="taxon:9606"
                     /chromosome="9"
                     /map="9q33"
     Protein         1..234
                     /product="CD30L protein"
     Region          104..220
                     /region_name="TNF"
                     /note="Tumor Necrosis Factor; TNF superfamily members
                     include the cytokines: TNF (TNF-alpha), LT
                     (lymphotoxin-alpha, TNF-beta), CD40 ligand, Apo2L (TRAIL),
                     Fas ligand, and osteoprotegerin (OPG) ligand; cd00184"
                     /db_xref="CDD:29146"
     Site            order(107,140,142,190,195)
```

Figure 8 (cont'd)

```
                     /site_type="other"
                     /note="trimer interface"
                     /db_xref="CDD:29146"
        Site         order(116..117,157,164,169)
                     /site_type="other"
                     /note="receptor binding sites"
                     /db_xref="CDD:29146"
        CDS          1..234
                     /gene="CD30L"
                     /coded_by="join(AF006381.1:1599..1793,AF006382.1:188..230,
                     AF006383.1:534..605,AF006384.1:347..741)"
ORIGIN
        1 mdpglqqaln gmappgdtam hvpagsvash lgttsrsyfy lttatlalcl vftvatimvl
       61 vvqrtdsipn spdnvplkgg ncsedllcil krapfkkswa ylqvakhlnk tklswnkdgi
      121 lhgvryqdgn lviqfpglyf iicqlqflvq cpnnsvdlkx ellinkhikk qxlvtvcesg
      181 mqtkhvyqnl sqflldylqv nttisvnvdt xqyidtstfp lenvlsiflx snsd
//
```

Disclaimer | Write to the Help Desk
NCBI | NLM | NIH

Figure 8 (cont'd)

```
                                                                    My N(
    NCBI                                      Protein     [Sign In] [Regis
    PubMed    Nucleotide   Protein   Genome   Structure   PMC   Taxonomy   OMIM   Books
Search Protein          for                                    [Go] [Clear]
            Limits      Preview/Index    History     Clipboard    Details
Display GenPept      Show 5    Send to Range: from |begin    to |end       Features: ☑CDD [+] [Refresh]
```

☐ 1: P42081. Reports T-lymphocyte acti...[gi:1168851]         BLink, Conserved
                                                              Domains, Links Comment    Features    Sequence

```
LOCUS       P42081                   329 aa            linear   PRI 15-JAN-2008
DEFINITION  T-lymphocyte activation antigen CD86 precursor (Activation B7-2
            antigen) (CTLA-4 counter-receptor B7.2) (B70) (FUN-1) (BU63).
ACCESSION   P42081
VERSION     P42081.1  GI:1168851
DBSOURCE    swissprot: locus CD86_HUMAN, accession P42081;
            class: standard.
            extra accessions:A0N0P0,Q13655,Q6FHB1,Q6GTS4,Q7M4L5
            created: Nov 1, 1995.
            sequence updated: Nov 1, 1995.
            annotation updated: Jan 15, 2008.
            xrefs: U04343.1, AAB03814.1, L25259.1, AAA58389.1, CR541844.1,
            CAG46642.1, EF064748.1, ABK41931.1, BC040261.1, AAH40261.1,
            U17722.1, AAA86473.1, U17717.1, U17718.1, U17719.1, U17721.1,
            A48754, JC7605, 1I85, 1NCN
            xrefs (non-sequence databases): UniGene:Hs.171182, PDBsum:1I85,
            PDBsum:1NCN, IntAct:P42081, Ensembl:ENSG00000114013, KEGG:hsa:942,
            H-InvDB:HIX0024331, HGNC:1705, HPA:CAB004319, MIM:601020,
            PharmGKB:PA26243, LinkHub:P42081, ArrayExpress:P42081,
            CleanEx:HS_CD86, GermOnline:ENSG00000114013, GO:0016021,
            GO:0005886, GO:0015026, GO:0005515, GO:0016563, GO:0007267,
            GO:0008284, GO:0045086, GO:0045404, GO:0043017, GO:0045630,
            GO:0045941, InterPro:IPR015651, InterPro:IPR007110,
            InterPro:IPR013783, InterPro:IPR003006, InterPro:IPR013106,
            InterPro:IPR003596, Gene3D:G3DSA:2.60.40.10,
            PANTHER:PTHR13712:SF45, Pfam:PF07686, SMART:SM00406,
            PROSITE:PS50835, PROSITE:PS00290
KEYWORDS    3D-structure; Alternative splicing; Glycoprotein; Host-virus
            interaction; Immunoglobulin domain; Membrane; Polymorphism;
            Receptor; Signal; Transmembrane; Ubl conjugation.
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (residues 1 to 329)
  AUTHORS   Azuma,M., Ito,D., Yagita,H., Okumura,K., Phillips,J.H., Lanier,L.L.
            and Somoza,C.
  TITLE     B70 antigen is a second ligand for CTLA-4 and CD28
  JOURNAL   Nature 366 (6450), 76-79 (1993)
  PUBMED    7694153
  REMARK    NUCLEOTIDE SEQUENCE [MRNA] (ISOFORM 2).
```

Figure 8 (cont'd)

```
REFERENCE   2  (residues 1 to 329)
  AUTHORS   Freeman,G.J., Gribben,J.G., Boussiotis,V.A., Ng,J.W., Restivo,V.A.
            Jr., Lombard,L.A., Gray,G.S. and Nadler,L.M.
  TITLE     Cloning of B7-2: a CTLA-4 counter-receptor that costimulates human
            T cell proliferation
  JOURNAL   Science 262 (5135), 909-911 (1993)
   PUBMED   7694363
  REMARK    NUCLEOTIDE SEQUENCE [MRNA] (ISOFORM 1).
REFERENCE   3  (residues 1 to 329)
  AUTHORS   Magistrelli,G., Caron,G., Gauchat,J.F., Jeannin,P., Bonnefoy,J.Y.
            and Delneste,Y.
  TITLE     Identification of an alternatively spliced variant of human CD86
            mRNA
  JOURNAL   Biochem. Biophys. Res. Commun. 280 (5), 1211-1215 (2001)
   PUBMED   11162656
  REMARK    NUCLEOTIDE SEQUENCE [MRNA] (ISOFORM 3).
REFERENCE   4  (residues 1 to 329)
  AUTHORS   Halleck,A., Ebert,L., Mkoundinya,M., Schick,M., Eisenstein,S.,
            Neubert,P., Kstrang,K., Schatten,R., Shen,B., Henze,S., Mar,W.,
            Korn,B., Zuo,D., Hu,Y. and LaBaer,J.
  TITLE     Direct Submission
  JOURNAL   Submitted (??-JUN-2004)
  REMARK    NUCLEOTIDE SEQUENCE [LARGE SCALE MRNA] (ISOFORM 2).
REFERENCE   5  (residues 1 to 329)
  AUTHORS   Livingston,R.J., Shaffer,T., McFarland,I., Nguyen,C.P.,
            Stanaway,I.B., Rajkumar,N., Johnson,E.J., da Ponte,S.H., Willa,H.,
            Ahearn,M.O., Bertucci,C., Acklestad,J., Carroll,A., Swanson,J.,
            Gildersleeve,H.I. and Nickerson,D.A.
  TITLE     Direct Submission
  JOURNAL   Submitted (??-OCT-2006)
  REMARK    NUCLEOTIDE SEQUENCE [GENOMIC DNA].
REFERENCE   6  (residues 1 to 329)
  AUTHORS   Gerhard,D.S., Wagner,L., Feingold,E.A., Shenmen,C.M., Grouse,L.H.,
            Schuler,G., Klein,S.L., Old,S., Rasooly,R., Good,P., Guyer,M.,
            Peck,A.M., Derge,J.G., Lipman,D., Collins,F.S., Jang,W., Sherry,S.,
            Feolo,M., Misquitta,L., Lee,E., Rotmistrovsky,K., Greenhut,S.F.,
            Schaefer,C.F., Buetow,K., Bonner,T.I., Haussler,D., Kent,J.,
            Kiekhaus,M., Furey,T., Brent,M., Prange,C., Schreiber,K.,
            Shapiro,N., Bhat,N.K., Hopkins,R.F., Hsie,F., Driscoll,T.,
            Soares,M.B., Casavant,T.L., Scheetz,T.E., Brown-stein,M.J.,
            Usdin,T.B., Toshiyuki,S., Carninci,P., Piao,Y., Dudekula,D.B.,
            Ko,M.S., Kawakami,K., Suzuki,Y., Sugano,S., Gruber,C.E.,
            Smith,M.R., Simmons,B., Moore,T., Waterman,R., Johnson,S.L.,
            Ruan,Y., Wei,C.L., Mathavan,S., Gunaratne,P.H., Wu,J., Garcia,A.M.,
            Hulyk,S.W., Fuh,E., Yuan,Y., Sneed,A., Kowis,C., Hodgson,A.,
            Muzny,D.M., McPherson,J., Gibbs,R.A., Fahey,J., Helton,E.,
            Ketteman,M., Madan,A., Rodrigues,S., Sanchez,A., Whiting,M.,
            Madari,A., Young,A.C., Wetherby,K.D., Granite,S.J., Kwong,P.N.,
            Brinkley,C.P., Pearson,R.L., Bouffard,G.G., Blakesly,R.W.,
            Green,E.D., Dickson,M.C., Rodriguez,A.C., Grimwood,J., Schmutz,J.,
            Myers,R.M., Butterfield,Y.S., Griffith,M., Griffith,O.L.,
            Krzywinski,M.I., Liao,N., Morin,R., Palmquist,D., Petrescu,A.S.,
            Skalska,U., Smailus,D.E., Stott,J.M., Schnerch,A., Schein,J.E.,
            Jones,S.J., Holt,R.A., Baross,A., Marra,M.A., Clifton,S.,
            Makowski,K.A., Bosak,S. and Malek,J.
  CONSRTM   MGC Project Team
  TITLE     The status, quality, and expansion of the NIH full-length cDNA
            project: the Mammalian Gene Collection (MGC)
  JOURNAL   Genome Res. 14 (10B), 2121-2127 (2004)
   PUBMED   15489334
```

Figure 8 (cont'd)

| | |
|---|---|
| REMARK | NUCLEOTIDE SEQUENCE [LARGE SCALE MRNA] (ISOFORM 1), AND VARIANT THR-310. |
| | TISSUE=Brain |
| | Erratum:[Genome Res. 2006 Jun;16(6):804. Morrin, Ryan [corrected to Morin, Ryan]] |
| REFERENCE | 7 (residues 1 to 329) |
| AUTHORS | Jellis,C.L., Wang,S.S., Rennert,P., Borriello,F., Sharpe,A.H., Green,N.R. and Gray,G.S. |
| TITLE | Genomic organization of the gene coding for the costimulatory human B-lymphocyte antigen B7-2 (CD86) |
| JOURNAL | Immunogenetics 42 (2), 85-89 (1995) |
| PUBMED | 7541777 |
| REMARK | NUCLEOTIDE SEQUENCE [GENOMIC DNA] OF 7-329. |
| | TISSUE=Foreskin |
| REFERENCE | 8 (residues 1 to 329) |
| AUTHORS | Lanier,L.L., O'Fallon,S., Somoza,C., Phillips,J.H., Linsley,P.S., Okumura,K., Ito,D. and Azuma,M. |
| TITLE | CD80 (B7) and CD86 (B70) provide similar costimulatory signals for T cell proliferation, cytokine production, and generation of CTL |
| JOURNAL | J. Immunol. 154 (1), 97-105 (1995) |
| PUBMED | 7527824 |
| REMARK | CHARACTERIZATION. |
| REFERENCE | 9 (residues 1 to 329) |
| AUTHORS | Engel,P., Gribben,J.G., Freeman,G.J., Zhou,L.J., Nozawa,Y., Abe,M., Nadler,L.M., Wakasa,H. and Tedder,T.F. |
| TITLE | The B7-2 (B70) costimulatory molecule expressed by monocytes and activated B lymphocytes is the CD86 differentiation antigen |
| JOURNAL | Blood 84 (5), 1402-1407 (1994) |
| PUBMED | 7520767 |
| REMARK | IDENTIFICATION AS CD86. |
| REFERENCE | 10 (residues 1 to 329) |
| AUTHORS | Goto,E., Ishido,S., Sato,Y., Ohgimoto,S., Ohgimoto,K., Nagano-Fujii,M. and Hotta,H. |
| TITLE | c-MIR, a human E3 ubiquitin ligase, is a functional homolog of herpesvirus proteins MIR1 and MIR2 and has similar activity |
| JOURNAL | J. Biol. Chem. 278 (17), 14657-14668 (2003) |
| PUBMED | 12582153 |
| REMARK | UBIQUITINATION, AND INTERACTION WITH MARCH8. |
| COMMENT | On or before Feb 27, 2007 this sequence version replaced gi:74721835, gi:74757610, gi:627415, gi:25392201. |
| | [FUNCTION] Receptor involved in the costimulatory signal essential for T-lymphocyte proliferation and interleukin-2 production, by binding CD28 or CTLA-4. May play a critical role in the early events of T-cell activation and costimulation of naive T-cells, such as deciding between immunity and anergy that is made by T-cells within 24 hours after activation. Isoform 2 interferes with the formation of CD86 clusters, and thus acts as a negative regulator of T-cell activation. |
| | [SUBUNIT] Interacts with MARCH8. Interacts with human herpesvirus 8 MIR2 protein (Probable). |
| | [SUBCELLULAR LOCATION] Membrane; Single-pass type I membrane protein. |
| | [ALTERNATIVE PRODUCTS] Event=Alternative splicing; Named isoforms=3; Name=1; IsoId=P42081-1; Sequence=Displayed; Name=2; IsoId=P42081-3; Sequence=VSP_023124; Name=3; Synonyms=CD86 deltaEC; IsoId=P42081-2; Sequence=VSP_009125. |
| | [TISSUE SPECIFICITY] Expressed by activated B-lymphocytes and monocytes. |
| | [PTM] Polyubiquitinated; which is promoted by MARCH8 and results in endocytosis and lysosomal degradation. |

Figure 8 (cont'd)

```
            [SIMILARITY] Contains 1 Ig-like C2-type (immunoglobulin-like)
            domain.
            [SIMILARITY] Contains 1 Ig-like V-type (immunoglobulin-like)
            domain.
            [WEB RESOURCE] Name=Wikipedia; Note=CD86 entry;
            URL='http://en.wikipedia.org/wiki/CD86'.
FEATURES             Location/Qualifiers
     source          1..329
                     /organism="Homo sapiens"
                     /db_xref="taxon:9606"
     gene            1..329
                     /gene="CD86"
                     /note="synonym: CD28LG2"
     Protein         1..329
                     /gene="CD86"
                     /product="T-lymphocyte activation antigen CD86 precursor"
     Region          1..23
                     /gene="CD86"
                     /region_name="Signal"
                     /inference="non-experimental evidence, no additional
                     details recorded"
                     /note="Potential."
     Region          1..6
                     /gene="CD86"
                     /region_name="Splicing variant"
                     /experiment="experimental evidence, no additional details
                     recorded"
                     /note="Missing (in isoform 2). /FTId=VSP_023124."
     Region          22..234
                     /gene="CD86"
                     /region_name="Splicing variant"
                     /experiment="experimental evidence, no additional details
                     recorded"
                     /note="Missing (in isoform 3). /FTId=VSP_009125."
     Region          24..329
                     /gene="CD86"
                     /region_name="Mature chain"
                     /experiment="experimental evidence, no additional details
                     recorded"
                     /note="T-lymphocyte activation antigen CD86.
                     /FTId=PRO_0000014550."
     Region          24..247
                     /gene="CD86"
                     /region_name="Topological domain"
                     /inference="non-experimental evidence, no additional
                     details recorded"
                     /note="Extracellular (Potential)."
     Region          27..31
                     /gene="CD86"
                     /region_name="Beta-strand region"
                     /experiment="experimental evidence, no additional details
                     recorded"
     Region          27
                     /gene="CD86"
                     /region_name="Conflict"
                     /experiment="experimental evidence, no additional details
                     recorded"
                     /note="K -> E (in Ref. 7; AAA86473)."
     Region          33..131
                     /gene="CD86"
```

Figure 8 (cont'd)

```
                    /region_name="Domain"
                    /experiment="experimental evidence, no additional details
                    recorded"
                    /note="Ig-like V-type."
Site                33
                    /gene="CD86"
                    /site_type="glycosylation"
                    /inference="non-experimental evidence, no additional
                    details recorded"
                    /note="N-linked (GlcNAc...) (Potential)."
Region              35..110
                    /gene="CD86"
                    /region_name="IGv"
                    /note="Immunoglobulin V-Type; smart00406"
                    /db_xref="CDD:47715"
Region              36..38
                    /gene="CD86"
                    /region_name="Beta-strand region"
                    /experiment="experimental evidence, no additional details
                    recorded"
Bond                bond(40,110)
                    /gene="CD86"
                    /bond_type="disulfide"
                    /inference="non-experimental evidence, no additional
                    details recorded"
                    /note="Potential."
Site                47
                    /gene="CD86"
                    /site_type="glycosylation"
                    /inference="non-experimental evidence, no additional
                    details recorded"
                    /note="N-linked (GlcNAc...) (Potential)."
Region              54..58
                    /gene="CD86"
                    /region_name="Beta-strand region"
                    /experiment="experimental evidence, no additional details
                    recorded"
Region              64..69
                    /gene="CD86"
                    /region_name="Beta-strand region"
                    /experiment="experimental evidence, no additional details
                    recorded"
Region              80..84
                    /gene="CD86"
                    /region_name="Hydrogen bonded turn"
                    /experiment="experimental evidence, no additional details
                    recorded"
Region              85..88
                    /gene="CD86"
                    /region_name="Beta-strand region"
                    /experiment="experimental evidence, no additional details
                    recorded"
Region              90..92
                    /gene="CD86"
                    /region_name="Hydrogen bonded turn"
                    /experiment="experimental evidence, no additional details
                    recorded"
Region              95..97
                    /gene="CD86"
```

Figure 8 (cont'd)

```
                  /experiment="experimental evidence, no additional details
                  recorded"
     Region       106..113
                  /gene="CD86"
                  /region_name="Beta-strand region"
                  /experiment="experimental evidence, no additional details
                  recorded"
     Region       122..133
                  /gene="CD86"
                  /region_name="Beta-strand region"
                  /experiment="experimental evidence, no additional details
                  recorded"
     Site         135
                  /gene="CD86"
                  /site_type="glycosylation"
                  /inference="non-experimental evidence, no additional
                  details recorded"
                  /note="N-linked (GlcNAc...) (Potential)."
     Site         146
                  /gene="CD86"
                  /site_type="glycosylation"
                  /inference="non-experimental evidence, no additional
                  details recorded"
                  /note="N-linked (GlcNAc...) (Potential)."
     Region       150..225
                  /gene="CD86"
                  /region_name="Domain"
                  /experiment="experimental evidence, no additional details
                  recorded"
                  /note="Ig-like C2-type."
     Site         154
                  /gene="CD86"
                  /site_type="glycosylation"
                  /inference="non-experimental evidence, no additional
                  details recorded"
                  /note="N-linked (GlcNAc...) (Potential)."
     Bond         bond(157,218)
                  /gene="CD86"
                  /bond_type="disulfide"
                  /inference="non-experimental evidence, no additional
                  details recorded"
                  /note="Potential."
     Region       170
                  /gene="CD86"
                  /region_name="Variant"
                  /experiment="experimental evidence, no additional details
                  recorded"
                  /note="S -> N (in dbSNP:rs9282642). /FTId=VAR_021916."
     Site         177
                  /gene="CD86"
                  /site_type="glycosylation"
                  /inference="non-experimental evidence, no additional
                  details recorded"
                  /note="N-linked (GlcNAc...) (Potential)."
     Site         192
                  /gene="CD86"
                  /site_type="glycosylation"
                  /inference="non-experimental evidence, no additional
                  details recorded"
                  /note="N-linked (GlcNAc...) (Potential)."
```

Figure 8 (cont'd)

```
     Site            213
                     /gene="CD86"
                     /site_type="glycosylation"
                     /inference="non-experimental evidence, no additional
                     details recorded"
                     /note="N-linked (GlcNAc...) (Potential)."
     Region          248..268
                     /gene="CD86"
                     /region_name="Transmembrane region"
                     /inference="non-experimental evidence, no additional
                     details recorded"
                     /note="Potential."
     Region          269..329
                     /gene="CD86"
                     /region_name="Topological domain"
                     /inference="non-experimental evidence, no additional
                     details recorded"
                     /note="Cytoplasmic (Potential)."
     Region          310
                     /gene="CD86"
                     /region_name="Variant"
                     /experiment="experimental evidence, no additional details
                     recorded"
                     /note="A -> T (in dbSNP:rs1129055). /FTId=VAR_014650."
     Region          323
                     /gene="CD86"
                     /region_name="Variant"
                     /experiment="experimental evidence, no additional details
                     recorded"
                     /note="D -> N (in dbSNP:rs9282648). /FTId=VAR_021917."
ORIGIN
        1 mdpqctmgls nilfvmafll sgaaplkiqa yfnetadlpc qfansqnqsl selvvfwqdq
       61 enlvlnevyl gkekfdsvhs kymgrtsfds dswtlrlhnl qikdkglyqc iihhkkptgm
      121 irihqmnsel svlanfsqpe ivpisniten vyinltcssi hgypepkkms vllrtknsti
      181 eydgimqksq dnvtelydvs islsvsfpdv tsnmtifcil etdktrllss pfsieledpq
      241 pppdhipwit avlptviicv mvfclilwkw kkkkrprnsy kcgtntmere eseqtkkrek
      301 ihipersdea qrvfksskts scdksdtcf
//
```

CONSTITUTIVE EXPRESSION OF COSTIMULATORY LIGANDS ON ADOPTIVELY TRANSFERRED T LYMPHOCYTES

CROSS-REFERENCE TO RELATED APPLICATIONS

This application is a divisional of U.S. application Ser. No. 14/734,969, filed on Jun. 9, 2015, which is a continuation of U.S. application Ser. No. 13/595,440, filed on Aug. 27, 2012, issued as U.S. Pat. No. 9,220,728, which is a divisional of U.S. application Ser. No. 12/593,751, filed Mar. 8, 2010, issued as U.S. Pat. No. 8,389,282, which is the U.S. national phase, pursuant to 35 U.S.C. § 371, of PCT international application Ser. No. PCT/US2008/004251, filed Mar. 31, 2008, designating the United States and published in English on Oct. 9, 2008 as publication WO 2008/121420 A1, which claims the benefit of U.S. provisional application Ser. No. 60/921,144, filed on Mar. 30, 2007, the contents of each of which are incorporated by reference in their entirety, and to each of which priority is claimed.

Each of the applications and patents cited in this text, as well as each document or reference cited in each of the applications and patents (including during the prosecution of each issued patent ("application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each documents or reference cited in each of the herein cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This invention was made with government support under grant number CA059350 awarded by the National Institutes of Health. The government has certain rights in the invention.

SEQUENCE LISTING

The specification further incorporates by reference the Sequence Listing submitted herewith via EFS on Sep. 19, 2018. Pursuant to 37 C.F.R. § 1.52(e)(5), the Sequence Listing text file, identified as "0727340788SEQLIST.TXT," is 14,545 bytes and was created on Sep. 19, 2018. The Sequence Listing, electronically filed herewith, does not extend beyond the scope of the specification and thus does not contain new matter.

BACKGROUND OF THE INVENTION

Prostate cancer is the most frequent cancer in males in the United States and the cause of nearly 31,000 deaths per year. When diagnosed early, cancer can be effectively treated by surgery or radiation. Postsurgical residual disease requires radiation and/or hormonal therapy, which may prevent tumor progression and metastasis. At present, there is no curative treatment for hormone refractory, metastatic prostate cancer. Immunotherapy is a targeted therapy that in principle provides for the treatment of such cancers. Obstacles remain to induce tumor immunity, which requires the expansion of cytotoxic T lymphocytes to numbers sufficient to mediate tumor rejection. Among the mechanisms limiting efficient T cell priming and tumor rejection is the inherent absence of costimulatory ligands on many malignancies.

SUMMARY OF THE INVENTION

The present invention generally provides immunoresponsive cells, including T cells and Natural Killer (NK) cells, expressing at least one of an antigen-recognizing receptor and a co-stimulatory ligand and methods of use therefore for the treatment of neoplasia, infectious disease, and other pathologies.

In one aspect, the invention generally provides an immunoresponsive cell comprising a receptor that binds an antigen and an exogenous co-stimulatory ligand.

In another aspect, the invention provides a virus specific T cell expressing a vector (e.g., an expression vector) encoding a polypeptide selected from any one or more of CD80, 4-1BBL, OX40L, CD70 and CD30L. In one embodiment, the virus specific T cell recognizes a virus selected from any one or more of Cytomegalovirus (CMV), Epstein Barr Virus (EBV), Human Immunodeficiency Virus (HIV), and influenza virus antigens.

In yet another aspect, the invention provides a tumor antigen-specific T cell expressing a vector encoding a polypeptide selected from the group consisting of CD80, 4-1BBL, OX40L, CD70 and CD30L. In one embodiment, the cell expresses CD80 and 4-1BBL. In another embodiment, the vector is a retroviral vector (e.g., gamma-retroviral or lentiviral); it may also be non-viral.

In yet another aspect, the invention provides a method of modulating an immune response in a subject, the method comprising administering an effective amount of an immunoresponsive cell of any previous aspect. In one embodiment, the method increases or reduces an immune response. In another embodiment, the method increases self-tolerance or increases tolerance to an organ transplant.

In yet another aspect, the invention provides a method of treating or preventing a neoplasia in a subject, the method comprising administering an effective amount of an immunoresponsive cell comprising a receptor that binds a tumor antigen and a vector encoding a co-stimulatory ligand. In one embodiment, the neoplasia is selected from the any one or more of prostate cancer, colon cancer, breast cancer, and glioblastoma. In another embodiment, the tumor antigen is prostate-specific membrane antigen, CD19, NY-ESO-1, WT-1, hTERT, or mesothelin.

In another aspect, the invention provides a method of enforcing tolerance in a subject, the method comprising administering an effective amount of an immunoresponsive cell comprising a receptor that binds an antigen and a vector encoding a co-stimulatory ligand. In one embodiment, the method prevents or reduces an autoimmune disease or a disease associated with allogeneic transplantation.

In yet another aspect, the invention provides a method of treating or preventing a pathogen infection in a subject, the method comprising administering an effective amount of an immunoresponsive cell comprising a receptor that binds a viral antigen and a vector encoding a co-stimulatory ligand.

In one embodiment, the pathogen is a virus, bacteria, fungus, protozoa or parasite. In another embodiment, the virus is selected from any one or more of Cytomegalovirus (CMV), Epstein Barr Virus (EBV), Human Immunodeficiency Virus (HIV), and influenza virus. In yet another embodiment, the cell is a T cell, a Natural Killer (NK) cell, or a cytotoxic T lymphocyte (CTL).

In still another aspect, the invention provides method for producing an antigen-specific immunoresponsive cell, the method comprising introducing into the immunoresponsive cell a nucleic acid sequence that encodes a chimeric antigen receptor, wherein the chimeric antigen receptor comprises an antigen-binding domain coupled to an intracellular signaling domain that activates an immunoresponsive cell. In one embodiment, the immunoresponsive cell is a T cell, CTL, or NK cell. In another embodiment, the antigen-binding domain is a tumor antigen-binding domain. In yet another embodiment, the tumor antigen is prostate specific membrane antigen (PSMA). In yet another embodiment, the intracellular signaling domain activates a T cell, CTL cell, or NK cell. In yet another embodiment, the intracellular signaling domain is the .zeta.-chain signaling domain.

In another aspect, the invention provides a method of treating a neoplasia in a subject in need thereof, the method comprising administering to the subject a therapeutically effective amount of a T cell comprising a tumor antigen and an antigen presenting complex comprising at least two co-stimulatory ligands, wherein at least one of the two co-stimulatory ligands is selected from any one or more of a tumor necrosis factor (TNF) ligand and an immunoglobulin (Ig) superfamily ligand and combinations thereof, thereby treating cancer in the subject.

In another aspect, the invention provides a method of treating a neoplasia in a subject, the method comprising administering to the subject a therapeutically effective amount of a Natural Killer (NK) cell comprising a tumor antigen and an antigen presenting complex comprising at least two co-stimulatory ligands, wherein at least one of the two co-stimulatory ligands is selected from any one or more of a tumor necrosis factor (TNF) ligand and an immunoglobulin (Ig) superfamily ligand and combinations thereof, thereby treating cancer in the subject. In one embodiment, the TNF ligand is selected from any one or more of 4-1BBL, OX40L, CD70, CD30L, and LIGHT. In another embodiment, the Ig superfamily ligand is selected from CD80 and CD86. In yet another embodiment, the cell expresses at least two co-stimulatory ligands, where one is a TNF ligand (e.g., 4-1BBL) and the other is an Ig superfamily ligand (e.g., CD80).

In another aspect, the invention provides a method of treating an infectious disease in a subject in need thereof, the method comprising administering to the subject a therapeutically effective amount of a T cell comprising a receptor specific for a viral antigen and an antigen presenting complex comprising at least two co-stimulatory ligands, wherein at least one of the two co-stimulatory ligands is selected from any one or more of a tumor necrosis factor (TNF) ligand and an immunoglobulin (Ig) superfamily ligand and combinations thereof, thereby treating the infectious disease in the subject.

In yet another aspect, the invention provides method of treating an infectious disease in a subject, comprising administering to the subject a therapeutically effective amount of a Natural Killer (NK) cell comprising a receptor specific for a viral antigen and an antigen presenting complex comprising at least two co-stimulatory ligands, wherein at least one of the two co-stimulatory ligands is selected from any one or more of a tumor necrosis factor (TNF) ligand and an immunoglobulin (Ig) superfamily ligand and combinations thereof, thereby treating the infectious disease in the subject. In one embodiment, the subject is an immunocompromised subject. In another embodiment, the TNF ligand is selected from any one or more of 4-1BBL, OX40L, CD70, LIGHT and CD30L. In yet another embodiment, the Ig superfamily ligand is selected from any one or more of CD80 and CD86. In yet another embodiment, the at least two co-stimulatory ligands are a TNF ligand and an Ig superfamily ligand. In another embodiment, the TNF ligand is 4-1BBL and the Ig superfamily ligand is CD80. In another embodiment, the antigen recognition complex is constitutively expressed on the surface of the cell. In another embodiment, the viral antigen is an antigen specific for Cytomegalovirus (CMV), Epstein Barr Virus (EBV), Human Immunodeficiency Virus (HIV), or influenza virus. In another embodiment, the at least two co-stimulatory ligands are constitutively expressed on the surface of the cell.

In another aspect, the invention provides a pharmaceutical composition comprising an effective amount of an immunoresponsive cell of any previous aspect in a pharmaceutically acceptable excipient.

In another aspect, the invention provides a pharmaceutical composition for the treatment of a neoplasia comprising an effective amount of a tumor antigen-specific T cell of any previous aspect in a pharmaceutically acceptable excipient.

In another aspect, the invention provides a pharmaceutical composition for the treatment of a pathogen infection comprising an effective amount of a viral-specific T cell of the previous aspect in a pharmaceutically acceptable excipient. In one embodiment, the composition further comprising a cytokine selected from any one or more of IL-2, IL-3, IL-6, IL-11, IL7, IL12, IL15, IL21, granulocyte macrophage colony stimulating factor, alpha, beta or gamma interferon and erythropoietin.

In another aspect, the invention provides a kit comprising an immunoresponsive cell comprising a receptor that binds an antigen and an exogenous co-stimulatory ligand. In one embodiment, the kit further comprises written directions for using said cell for the treatment of a subject having neoplasia, a pathogen infection, an autoimmune disorder, or an allogeneic transplant.

In various embodiments of any previous aspect, the method further comprises the step of obtaining the immunoresponsive cell or co-stimulatory ligand. In still other embodiments of the previous aspects, the co-stimulatory ligand is constitutively or inducibly expressed. In yet other embodiments of the previous aspects, at least two co-stimulatory ligands are constitutively expressed. In various embodiments of any previous aspect, the cell is selected from any one or more of of a T cell, a Natural Killer (NK) cell, a cytotoxic T lymphocyte (CTL), and a regulatory T cell. In still other embodiments of the previous aspects, the antigen is a tumor or pathogen antigen, e.g., any one or more of prostate-specific membrane antigen (PSMA), Carcinoembryonic Antigen (CEA), IL13Ralpha, her-2, CD19, NY-ESO-1, HIV-1 Gag, Lewis Y, Mart-1, gp100, tyrosinase, WT-1, hTERT, mesothelin. In still other embodiments of the previous aspects, the cell expresses a recombinant and/or an endogenous antigen receptor. In still other embodiments of the previous aspects, the co-stimulatory ligand is a tumor necrosis factor (TNF) ligand (e.g., 4-1BBL, OX40L, CD70, LIGHT, and CD30L) or an immunoglobulin (Ig) superfamily ligand (e.g., CD80 and CD86). In still other embodiments of the previous aspects, the immunoresponsive cell expresses at least one TNF ligand and at least one Ig superfamily ligand. In still other embodiments of the previous aspects, the cell expresses 4-1BBL and CD80. In still other embodiments of the previous aspects, an antigen presenting complex and/or co-stimulatory ligands are constitutively or inducibly expressed on the surface of the T cell. In still other embodiments of the previous aspects, the co-stimulatory ligand is expressed in a retroviral vector. In another embodiment, the tumor antigen is prostate-specific membrane antigen, CD19, NY-ESO-1, WT-1 or hTERT. In still other embodiments, the cell expresses a recombinant or an endogenous receptor for the antigen. In still other embodiments, the co-stimulatory ligand is a tumor necrosis factor (TNF) ligand or an immunoglobulin (Ig) superfamily ligand. In still other embodiments, the TNF ligand is selected from any one or more of 4-1BBL, OX40L, CD70, LIGHT, and CD30L. In various embodiments, the intracellular signaling domain is a ξ-chain signaling domain. In other embodiments, in the one costimulatory signal is provided through an engineered antigen receptor and the other by overexpressing a costimulatory ligand. In still other embodiments, the Ig superfamily ligand is selected from the group consisting of CD80 and CD86.

Definitions

By "CD80 polypeptide" is meant a protein having at least 85% identity to NCBI Reference No: NP 005182 or a fragment thereof that acts as an Ig superfamily ligand.

By "CD80 nucleic acid molecule" is meant any polynucleotide encoding a CD80 polypeptide. An exemplary CD80 nucleic acid molecule is NM.sub.-005191.

By "4-1BBL polypeptide" is meant a protein having at least 85% identity to NCBI Reference No: P41273 or NP 001552 or a fragment thereof that that acts as a tumor necrosis factor (TNF) ligand.

By "4-1BBL nucleic acid molecule" is meant a polynucleotide encoding a 4-1BBL polypeptide.

By "OX40L polypeptide" is meant a protein having at least 85% identity to NCBI Reference No:
BAB 18304 or NP 003317 or a fragment thereof that is a tumor necrosis factor (TNF) ligand.

By "OX40L nucleic acid molecule" is meant a polynucleotide encoding a OX40L polypeptide.

By "CD70 polypeptide" is meant a protein having at least 85% identity to NCBI Reference No: NP.sub.-001243 or a fragment thereof that acts as a tumor necrosis factor (TNF) ligand.

By "CD70 nucleic acid molecule" is meant a polynucleotide encoding a CD70 polypeptide.

By "Light polypeptide" is meant a protein having at least 85% identity to NCBI Reference No: NP 742011 or a fragment thereof that acts as a tumor necrosis factor (TNF) ligand.

By "Light nucleic acid molecule" is meant a polynucleotide encoding a Light polypeptide.

By "CD30L polypeptide" is meant a protein having at least 85% identity to NCBI Reference No: AAB97877 or a fragment thereof that acts as a tumor necrosis factor (TNF) ligand.

By "CD30L nucleic acid molecule" is meant a polynucleotide encoding a CD30L polypeptide.

By "CD86 polypeptide" is meant a protein having at least 85% identity to NCBI Reference No: P42081 or a fragment thereof that acts as an Ig superfamily ligand.

By "CD86 nucleic acid molecule" is meant a polynucleotide encoding a CD86 polypeptide.

By "Pz1 polypeptide" is meant a protein having at least 85% identity to the protein described by Gong et al., Neoplasia 1:123-7, 1999 or a fragment thereof.

By "P28z polypeptide" is meant a protein having at least 85% identity to the protein described by Maher et al. Nature Biotechnology, Vol 20, January 2002, 70-75 or a fragment thereof. The .zeta.-chain signaling domain is also described by Maher et al. Nature Biotechnology, Vol 20, January 2002, 70-75.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule. The term "ligand" as used herein refers to a molecule that binds to a receptor. In particular, the ligand binds a receptor on another cell, allowing for cell-to-cell recognition.

The term "constitutive expression" as used herein refers to expression under all physiological conditions.

The term "chimeric antigen receptor" (CAR) as used herein refers to a tumor antigen-binding domain that is fused to an intracellular signaling domain capable of activating T cells. Most commonly, the CAR's extracellular binding domain is derived from a murine or humanized monoclonal antibody.

By "disease" is meant any condition or disorder that damages or interferes with the normal function of a cell, tissue, or organ. Examples of diseases include neoplasia or pathogen infection of cell.

By "effective amount" is meant an amount sufficient to arrest, ameliorate, or inhibit the continued proliferation, growth, or metastasis (e.g., invasion, or migration) of a neoplasia.

By "enforcing tolerance" is meant preventing the activity of self-reactive cells or immunoresponsive cells that target transplanted organs or tissues.

By "exogenous" is meant a nucleic acid molecule or polypeptide that is not endogenously present in the cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample. By "immunoresponsive cell" is meant a cell that functions in an immune response or a progenitor, or progeny thereof.

By "isolated cell" is meant a cell that is separated from the molecular and/or cellular components that naturally accompany the cell.

The term "tumor antigen-binding domain" as used herein refers to a domain capable of specifically binding a particular antigenic determinant or set of antigenic determinants present on a tumor.

The term "obtaining" as in "obtaining the agent" is intended to include purchasing, synthesizing or otherwise acquiring the agent (or indicated substance or material).

By "modulate" is meant positively or negatively alter. Exemplary modulations include a 1%, 2%, 5%, 10%, 25%, 50%, 75%, or 100% change.

By "neoplasia" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells). Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma. In one embodiment, screening methods of the invention identify compositions that are useful for treating breast or lung cancer.

By "receptor" is meant a polypeptide, or portion thereof, present on a cell membrane that selectively binds one or more ligand.

By "recognize" is meant selectively binds a target. A T cell that recognizes a virus typically expresses a receptor that binds an antigen expressed by the virus.

By "pathogen" is meant a virus, bacteria, fungi, parasite or protozoa capable of causing disease.

Exemplary viruses include, but are not limited to, *Retroviridae* (e.g. human immunodeficiency viruses, such as HIV-1 (also referred to as HDTV-III, LAVE or HTLV-III/LAV, or HIV-III; and other isolates, such as HIV-LP; *Picornaviridae* (e.g. polio viruses, hepatitis A virus; enteroviruses, human Coxsackie viruses, rhinoviruses, echoviruses); *Calciviridae* (e.g. strains that cause gastroenteritis); *Togaviridae* (e.g. equine encephalitis viruses, rubella viruses); *Flaviridae* (e.g. dengue viruses, encephalitis viruses, yellow fever viruses); *Coronoviridae* (e.g. coronaviruses); *Rhabdoviridae* (e.g. vesicular stomatitis viruses, rabies viruses); *Filoviridae* (e.g. ebola viruses); *Paramyxoviridae* (e.g. parainfluenza viruses, mumps virus, measles virus, respiratory syncytial virus); *Orthomyxoviridae* (e.g. influenza viruses); *Bungaviridae* (e.g. Hantaan viruses, bunga viruses, phleboviruses and Nairo viruses); Arena viridae (hemorrhagic fever viruses); *Reoviridae* (e.g. reoviruses, orbiviurses and rotaviruses); *Birnaviridae; Hepadnaviridae* (Hepatitis B virus); *Parvovirida* (parvoviruses); *Papovaviridae* (papilloma viruses, polyoma viruses); *Adenoviridae* (most adenoviruses); *Herpesviridae* (herpes simplex virus (HSV) 1 and 2, varicella zoster virus, cytomegalovirus (CMV), herpes virus; *Poxviridae* (variola viruses, vaccinia viruses, pox viruses); and *Iridoviridae* (e.g. African swine fever virus); and unclassified viruses (e.g. the agent of delta hepatitis (thought to be a defective satellite of hepatitis B virus), the agents of non-A, non-B hepatitis (class 1=internally transmitted; class 232 parenterally transmitted (i.e. Hepatitis C); Norwalk and related viruses, and astroviruses).

Exemplary bacteria include, but are not limited to, *Pasteurella, Staphylococci, Streptococcus, Escherichia coli, Pseudomonas species,* and *Salmonella* species. Specific examples of infectious bacteria include but are not limited to, *Helicobacter pyloris, Borelia burgdorferi, Legionella pneumophilia, Mycobacteria* sps (e.g. *M tuberculosis, M avium, M intracellulare, M kansaii, M gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli.*

By "specifically binds" is meant a polypeptide or fragment thereof that recognizes and binds a polypeptide of interest, but which does not substantially recognize and bind other molecules in a sample, for example, a biological sample, which naturally includes a polypeptide of the invention.

The term "tumor antigen" as used herein refers to any polypeptide expressed by a tumor that is capable of inducing an immune response.

By "virus antigen" is meant a polypeptide expressed by a virus that is capable of inducing an immune response.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

The term "subject" as used herein refers to a vertebrate, preferably a mammal, more preferably a human.

The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the invention are described in the following disclosure and are within the ambit of the invention.

BRIEF DESCRIPTION OF THE FIGURES

The following Detailed Description, given by way of example, but not intended to limit the invention to specific embodiments described, may be understood in conjunction with the accompanying figures.

FIGS. 1a-1f show that CD80 and 4-1BBL co-expression in human T-cells elicits robust proliferative responses after cyclic stimulations through their endogenous T cell receptor or through a chimeric antigen receptor without antigen presenting cell (APC)-provided costimulation. $0.4 \times 10^6$ purified human T lymphocytes was activated with antibody to CD3 (OKT3) and quantified the expansion of T lymphocytes retrovirally transduced with CD80, 4-1BBL, the combination of the two, or a control vector (FIG. 1a,b) Transduction efficiencies were assessed by FACS analysis 48 h after gene transfer (FIG. 1a). The absolute count of $CD8^+$ T cells transduced with the indicated costimulatory ligand and stimulated weekly with 10 .mu.g/ml plate-bound OKT3 is graphed in FIG. 1b. The investigation was extended to Cytomegalovirus (CMV)-specific memory donor T cells (FIG. 1c,d) and genetically redirected autologous T cells (FIG. 1e,f). CMV-pp65-specific T lymphocytes, briefly expanded on HLA-A*0201$^+$pp65$^+$ artificial APCs and transduced with CD80, 4-1BBL, or a combination of the two (FIG. 1c). Absolute counts of $CD8^+pp65^+$ T cells enriched and transduced as described in c after weekly restimulation with HLA-A*0201+ pp65-presenting Caco-2 tumor cells are shown in FIG. 1d. To rapidly generate prostate cancer-reactive human T lymphocytes (FIG. 1e,f), peripheral blood T cells were retrovirally transduced with the chimeric antigen receptor Pz1 (Gade et al., Cancer Res. 65:9080-9088, 2005), a non-HLA restricted antigen receptor specific for the tumor antigen PSMA. The Pz1 receptor comprises a PSMA-binding single-chain antibody fragment fused to the human CD3 .zeta. signaling domain. In FIG. 1e, primary human CD3+T lymphocytes was retrovirally transduced with Pz1 alone or in combination with CD80 and 4-1BBL. Transduction efficiencies were assessed by FACS analysis. The T cell expansion of Pz1-transduced human T lymphocytes cocultured weekly with LNCaP tumor monolayers is shown in FIG. 1f. Costimulatory ligands were expressed on the T cell (top) or the tumor cell (bottom). Respective activation condition are depicted in cartoons shown in the right panels of b,d and f. Data are representative of three independent experiments. Each point in b, d and f represents the mean ±s.e.m. of three randomly picked wells. * indicates <$10^4$ cells.

FIGS. 2a-2c show the eradication of established—prostate-specific membrane antigen (PSMA) prostate carcinoma tumors in Scid/beige mice by Pz1+ T-cells transduced with CD80 and 4-1BBL. FIG. 2a shows in vivo bioluminescent imaging and corresponding coronal MRI scans of firefly luciferase +PC3-PSMA tumors in Scid/beige mice four weeks after systemic inoculation with $4 \times 10^6$ tumor cells (day 0 of T-cell treatment), and eighteen days after adoptive transfer of $4 \times 10^6$ CD8+Pz1+ or Pz1+CD80+4-1BBL+ T lymphocytes. An equal number of T-cells bearing the human CD19-targeting chimeric antigen receptor 19z were injected in the control group. Pseudocolor images superimposed on conventional photographs are shown. The same animals imaged before and after treatment using bioluminescent imaging and MRI are shown. The two mice represent a total of n=10. FIG. 2b shows three graphs. Bioluminescent tumor signal quantified per animal every two days over a time period of 28 days. Acquisitions with saturated pixels—although included in the figure to allow direct visual comparison between groups—were not used for photon quantification but repeated at a shorter acquisition time. The graph shows photons/second/$cm^2$/surface radius (sr) versus days after T cell injection. Every line corresponds to one animal with each dot representing the average photon count of the ventral and dorsal acquisition per animal at any given time point. Survival is illustrated in the Kaplan-Meier curve in FIG. 2c.

FIGS. 3a-3d show robust, yet tumor antigen dependent, in vivo proliferation of CD80+4-1BBL+ T lymphocytes. FIG. 3a shows comparative in vivo bioluminescent imaging of adoptively transferred T cells in PC3-PSMA tumor bearing Scid/beige mice on days 0, 8 and 18 after the injection of $4 \times 10^6$ CD8+ clickbeetle luciferase (click-luc)-expressing Pz1-transduced or Pz1+CD80+4-1BBL+ transduced T-lymphocytes. As an antigen specificity control, an equal number of 19z+CD80+4-1BBL+ T cells were infused. T-cell treatment started as in FIG. 2 four weeks after the systemic injection of $4 \times 10^6$ PC3-PSMA tumor cells. The five mice per group shown in each panel represent a total of n=8/group. Acquisitions with saturated pixels—although shown in the figure to allow direct visual comparison were not used for photon quantification but repeated at a shorter acquisition time. FIG. 3b shows three graphs. Clickbeetle luciferase signal intensities from sequential bioluminescence imaging were collected every 2 days after T-cell transfer over a sixteen day time period. Every line represents one animal with each dot showing the average photon count of the ventral and dorsal acquisition per animal at any given time point. FIG. 3c shows a multicolor FACS analysis of a lung single-cell suspension prepared from a representative animal infused either with Pz1+ or Pz1+CD80+4-1BBL+ T lymphocytes, 6 d after T cell transfer. Cells were stained with idiotypic antiserum specific for the chimeric antigen receptor Pz1. In FIG. 3d absolute pulmonary Pz1+ T cell numbers (total cell counts of viable Trypan blue-negative cells.times..percentages of Pz1+ T cells). Shown bar graphs represent the mean±s.e.m. of three mice.

In FIG. 4a-d, peripheral blood human T lymphocytes were transduced with Pz1 and restimulated with LNCaP-CD80 cells before a second gene transfer with the bicistronic vector encoding the dsRed-monomer-4-1BBL fusion protein and CD80. After negative magnetic CD8+ isolation, T cells were labeled with FITC-Choleratoxin B (CTB), and incubated with unmodified LNCaP tumor cells or alone. Fixed conjugates were permeabilized, stained with the indicated antisera and visualized by confocal microscopy. T cell-LNCaP cell clusters from three independent experiments were randomly chosen. Scale bars, 10 μm. The numbers of clusters with clear concentrations of the indicated costimulatory ligand or receptor at the T cell-APC junction over the total number of analyzed clusters is shown in the lower right panels of FIG. 4a and b. FIG. 4a is a set of ten confocal micrographs exemplifying the polarization of 4-1BBL—expressed as a ds-Red fusion protein in combination with CD80 on CD8+ Pz1 transduced T cells—into the immunological synapse. T-cell/LnCaP tumor clusters were incubated for 50 minutes before fixation, permeabilization and incubation with anti 4-1BB antiserum. In FIG. 4b, fixed T cell-tumor cell clusters were incubated with anti-CD80 and anti-CD28 antisera. Again, colocalization of CD80 with its receptor CD28 in the immunological synapse after tumor antigen encounter is visualized. FIG. 4c illustrates the augmented accumulation of granzyme-B at the immunological synapse. This accumulation is dependent on a functional engagement of 4-1BB by its ligand 4-1BBL, which is expressed on the same T cell surface. Primary human T lymphocytes were genetically modified as in FIG. 4a, b. As indicated, retroviral vectors encoding Pz1 also express control shRNA or 4-1BB targeting shRNA under the control of the U6 promoter in their 3'LTR as described herein below. Cell conjugates in the top (Pz1+control shRNA) and middle (and Pz1+CD80+dsred 4-1BBL+ control shRNA) row represent CD80+dsred 4-1BBL- untransduced and transduced T-lymphocytes, respectively, cultured in the same well and conjugated to LnCaP on the same glass slide. FIG. 4d shows the relative recruitment index (RRI) and the relative intensity, calculated as described herein below, of Granzyme-B-Alexa 647 at the T cell-antigen presenting cell interphase. Data points in each group show the calculated value of 35 analyzed conjugates (symbols) and their mean (—) of three independent experiments. *P=0.0001; **P<0.0001. In FIG. 4e,f, show NF-κB-luciferase assays in isolated single T cell clones. These results corroborate autocostimulation as an operant mechanism of delivering costimulatory signals. A CD3+CD28+4-1BB- Jurkat T cell clone stably transfected with an NF-κB-luciferase reporter was retrovirally transduced with a tricistronic vector coexpressing 4-1BB, 4-1BBL and CD80 or a control vector. To preclude bystander costimulation, transduced T lymphocytes were subcloned into OKT-3- coated 96-well plates before the first detectable surface IO expression of encoded proteins. Twelve hours after activation, the presence of single T cells in the wells was microscopically confirmed and the bioluminescent signal was measured on a single-cell level. FIG. 4e shows 36 bioluminescence acquisitions of transduced single T cells assembled with Adobe Illustrator software. Respective bioluminescent single-cell signals were quantified, normalized to background bioluminescence, and plotted in FIG. 4f.

FIG. 5a shows a set of 4 confocal micrographs of a Pz1$^+$ T cell engaging an LNCaP tumor cell while in physical T cell-Tcell contact with a bystander Pz1$^+$ T lymphocyte transduced with CD80 and dsRed-4-1BBL. Cell clusters were induced and analyzed as described in FIGS. 4a and 3b. Scale bars, 10 μm. In FIG. 5b-d, peripheral T lymphocytes of a cytomegalovirus (CMV)-seropositive HLA A2.1$^+$donor were transduced with Pz1 or co-transduced with Pz1, CD80 and 4-1BBL. In parallel, CMV-specific, genetically unmodified cytotoxic T lymphocytes (CTLs) from the same donor were enriched by artificial antigen presenting cell (AAPC) co-culture as described herein below. These cells were labeled with carboxyfluoroscein succinimidyl ester (CFSE). Bead-sorted Pz1$^+$ (FIG. 5b) or Pz1$^+$ CD80$^+$4-1BBL$^+$ (FIG. 5c) T lymphocytes were admixed to expanded CMV-reactive pp65$^+$ CTLs at a 1:1 ratio and exposed to irradiated Caco-2 tumor cells retrovirally transduced to present surface pp65 in an HLA A2.1-dependent, as well as PSMA in an HLA-independent manner. Alternatively, a transwell membrane separated Pz1$^+$CD80$^+$4-1BBL$^+$ T-cells from pp65$^+$ T-cells, both engaging Caco-2 tumor (FIG. 5d). Respective co-culture conditions are depicted in cartoons shown on the left. Two days after tumor antigen contact intracellular Granzyme B levels gated on CD8$^+$ T-cells were quantified by FACS analysis (middle column). Granzyme B-antigen presenting cell (APC) mean fluorescent intensities (MFI) of the CFSE (Pz1$^+$) and CFSE$^+$ (pp65$^+$) T cell sub-populations are summarized on top of each profile. On day 7 CFSE dilutions and Pz1$^+$ compared to pp65$^+$ T-cell fractions were analyzed by flow cytometry after pp65 tetramer and CD8 staining (right column)). CFSE-MFIs indicated on top of each profile are based on pp65$^+$-populations after CD8$^+$-gating. Total cell counts of CD8$^+$pp65$^+$ T-cells after the 7 day cultures are graphed in (FIG. 5e). Each bar graph represents the mean ±s.e.m of three randomly chosen wells. Data are representative of two independent experiments. No exogenous cytokines were added at any point of the co-culture.

FIG. 6a shows dual in vivo bioluminescence imaging of external Gaussia luciferase (x-gaus-luc) in RM1.PGLS and Raji tumors in addition to Clickbeetle luciferase (Click-luc) in tumor targeting T-cells. Two weeks after the systemic injection of 1×10$^6$ CD19$^+$x-gaus-luc$^+$ Raji tumors and two days after the subsequent infusion of 5×10$^5$ PSMA$^+$x-gaus-luc$^+$RM1.PGLS tumor cells into the same animals, established tumors in the bone marrow (Raji) and lung (RM1) were treated with a combination of three cell populations of T cells transduced as indicated. Each animal received a total of 12×10$^6$ CD8$^+$ chimeric antigen receptor$^+$ T-cells (4×10$^6$ T-cells/transduction condition). Notably, the T-cell population listed third (Pz1$^+$, Pz1$^+$CD80$^+$4-1BBL$^+$, 19z$^+$CD80$^+$4-1BBL$^+$, left, middle, right row, respectively) were injected twelve hours after the combined injection of T-cells listed first and second to avoid T-cell/T-cell interaction in the lung due to crowding and not as a result of selective tumor antigen binding. At the indicated time points x-gaus-luc" tumor cells or click-luc$^+$ T-cells were monitored by bioluminescent imaging. On day 0 and day 4 a time period of at least 4 hours between tumor and T-cell imaging ensured the bioluminescent signal to return to background levels. A total number of n=5 Scid/beige mice were imaged per treatment group. FIG. 6b shows a series of 6 graphs quantitating clickbeetle luciferase signal intensities from sequential bioluminescence imaging every day after T-cell transfer for a four day time period. Every line represents one animal with each dot showing the average photon count measured over the pulmonary area (top) or both femurs (bottom), respectively at any given time point.

DETAILED DESCRIPTION OF THE INVENTION

Figure 1A:
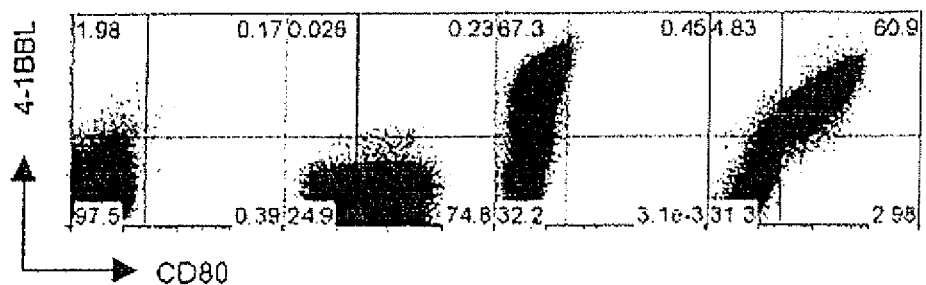

The present invention generally provides cells, including genetically modified immunoresponsive cells (e.g., T cells, Natural Killer (NK) cells, cytotoxic T lymphocytes (CTL) cells) expressing at least one of an antigen-recognizing receptor and a co-stimulatory ligand and methods of use therefore for the treatment of neoplasia and other pathologies where an increase in an antigen-specific immune response is desired. The invention is based, at least in part, on the discovery that the constitutive retroviral expression of CD80 and 4-1BBL in co-transduced human T cells targeting prostate specific membrane antigen mounted a robust tumor-antigen-dependent T-cell proliferation coupled with a profound in vivo rejection of disseminated well-established prostate carcinoma tumors. Furthermore, CD80 and 4-1BBL expressing T cells provided costimulation of bystander T cells in trans in a contact dependent and antigen-specific manner at the tumor site. Taken together, the concept of genetically modified T cells as a constitutive pool of costimulatory ligands to optimally costimulate themselves in addition to enhancing the immunogenicity within the tumor microenvironment represents a significant advance over conventional adoptive T cell therapy. Furthermore, as demonstrated ex vivo using enriched CMV-specific T lymphocytes, this approach is not limited to the treatment of neoplasias, but is amenable to a wide range of applications where an increase in an antigen-specific immune response is desired, such applications include not only the treatment of neoplasias, but also for the enhancement of an immune response against a pathogen infection or an infectious disease and to reinforce immune tolerance in regulatory T cells in the context of autoimmunity or allogeneic transplantation.

Hematopoietic Cell Lineages

Mammalian hematopoietic (blood) cells provide a diverse range of physiologic activities. Hematopoietic cells are divided into lymphoid, myeloid and erythroid lineages. The lymphoid lineage, comprising B, T and natural killer (NK) cells, provides for the production of antibodies, regulation of the cellular immune system, detection of foreign agents in the blood, detection of cells foreign to the host, and the like. The term "T cells" as used herein refers to lymphocytes that mature in the thymus and are chiefly responsible for cell-mediated immunity. T cells are involved in the adaptive immune system. The term "natural killer (NK) cells" as used herein refers to lymphocytes that are part of cell-mediated immunity and act during the innate immune response. They do not require prior activation in order to perform their cytotoxic effect on target cells. Cytotoxic T cells (CTL or killer T cells) are a subset of T lymphocytes capable of inducing the death of infected somatic or tumor cells.

Cells for Use in the Methods of the Invention

The present invention provides cells expressing at least one of an antigen-recognizing receptor and a co-stimulatory ligand and methods of using such cells for the treatment of a disease that requires an enhanced immune response. In one approach, tumor antigen-specific T cells, NK cells, CTL cells or other immunoresponsive cells are used as shuttles for the selective enrichment of one or more co-stimulatory ligands for the treatment or prevention of neoplasia. For example, a T cell expressing a co-stimulatory ligands 4-1BBL and CD80 are constitutively co-expressed in a T cell that expresses a chimeric antigen receptor PZ1 that recognizes and binds Prostate Specific Membrane Antigen (PSMA). Such cells are administered to a human subject in need thereof for the treatment or prevention of prostate cancer. In another approach, viral antigen-specific T cells, NK cells, CTL cells can be used for the treatment of viral diseases. For example, CD80 and 4-1BBL are expressed in cytomegalovirus (CMV)-specific cytotoxic T lymphocytes for the treatment of CMV.

Tumor Antigen-Specific T Lymphocytes (and NK Cells)

Types of tumor antigen-specific human lymphocytes that can be used in the methods of the invention include, without limitation, peripheral donor lymphocytes genetically modified to express chimeric antigen receptors (CARs) (Sadelain, M., et al. 2003 Nat Rev Cancer 3:35-45), peripheral donor lymphocytes genetically modified to express a full-length tumor antigen-recognizing T cell receptor complex comprising the α and β heterodimer (Morgan, R. A., et al. 2006 Science 314:126-129), lymphocyte cultures derived from tumor infiltrating lymphocytes (TILs) in tumor biopsies (Panelli, M. C., et al. 2000 J Immunol 164:495-504; Panelli, M. C., et al. 2000 J Immunol 164:4382-4392), and selectively in vitro-expanded antigen-specific peripheral blood leukocytes employing artificial antigen-presenting cells (AAPCs) or pulsed dendritic cells (Dupont, J., et al. 2005 Cancer Res 65:5417-5427; Papanicolaou, G A., et al. 2003 Blood 102:2498-2505). The T cells may be autologous, allogeneic, or derived in vitro from engineered progenitor or stem cells.

Any suitable tumor antigen (antigenic peptide) is suitable for use in the tumor-related embodiments described herein. Sources of antigen include, but are not limited to cancer proteins. The antigen can be expressed as a peptide or as an intact protein or portion thereof. The intact protein or a portion thereof can be native or mutagenized. One suitable antigen is prostate specific membrane antigen (PSMA).

Viral Antigen-Specific T Lymphocytes (and NK Cells)

Suitable antigens for use in the treatment of pathogen infection or other infectious disease, for example, in an immunocompromised subject include, without limitation, viral antigens present in Cytomegalovirus (CMV), Epstein Barr Virus (EBV), Human Immunodeficiency Virus (HIV), and influenza virus.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

Accordingly, the invention generally provides an immunoresponsive cell, such as a virus or tumor specific T cell comprising a receptor that binds an antigen and an exogenous co-stimulatory ligand (e.g., CD80, 4-1BBL, OX40L, CD70 and CD30L).

Vectors

Genetic modification of immunoresponsive cells (e.g., T cells, CTL cells, NK cells) can be accomplished by transducing a substantially homogeneous cell composition with a recombinant DNA construct. Preferably, a retroviral vector (either gamma-retroviral or lentiviral) is employed for the introduction of the DNA construct into the cell. For example, a polynucleotide encoding a co-stimulatory ligand protein (e.g., tumor necrosis factor (TNF) ligand, such as 4-1BBL, OX40L, CD70, LIGHT, and CD30L, or an Ig superfamily ligand, such as CD80 and CD86), or a receptor that binds an antigen, or a variant, or a fragment thereof, can be cloned into a retroviral vector and expression can be driven from its endogenous promoter, from the retroviral long terminal repeat, or from a promoter specific for a target cell type of interest. Non-viral vectors may be used as well.

Co-Stimulatory Ligands

The interaction with at least one co-stimulatory ligand provides a non-antigen-specific signal required for full activation of a T cell. Co-stimulatory ligands include, without limitation, tumor necrosis factor (TNF) ligands, cytokines (such as IL-2, IL-12, IL-15 or IL21), and immunoglobulin (Ig) superfamily ligands.

TNF Ligands

Tumor necrosis factor (TNF) is a cytokine involved in systemic inflammation and stimulates the acute phase reaction. Its primary role is in the regulation of immune cells. Tumor necrosis factor (TNF) ligands share a number of common features. The majority of the ligands are synthesized as type II transmembrane proteins (extracellular C-terminus) containing a short cytoplasmic segment and a relatively long extracellular region. TNF ligands include, without limitation, nerve growth factor (NGF), CD40L (CD40L)/CD154, CD137L/4-1BBL, tumor necrosis factor alpha (TNFα), CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF 14).

Ig Superfamily Ligands

The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80 and CD86, both ligands for CD28.

For initial genetic modification of the cells to provide tumor or viral antigen-specific cells, a retroviral vector is generally employed for transduction, however any other suitable viral vector or delivery system can be used. For subsequent genetic modification of the cells to provide cells comprising an antigen presenting complex comprising at least two co-stimulatory ligands, retroviral gene transfer (transduction) likewise proves effective. Combinations of retroviruses and an appropriate packaging line are also suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to express a co-stimulatory ligand of the invention in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adeno-viral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAF dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above. The resulting cells can then be grown under conditions similar to those for unmodified cells, whereby the modified cells can be expanded and used for a variety of purposes.

Polypeptides and Analogs

Also included in the invention are PZ1, P28z, 4-1BBL, OX40lL, CD70, LIGHT, and CD30L polypeptides or fragments thereof that are modified in ways that enhance their anti-neoplastic activity when expressed in an immunoresponsive cell. The invention provides methods for optimizing an amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both.

Analogs of the invention will generally exhibit at least 85%, more preferably 90%, and most preferably 95% or even 99% identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between e-3 and e-100 indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., $\beta$ or $\gamma$ amino acids.

In addition to full-length polypeptides, the invention also provides fragments of any one of the polypeptides or peptide domains of the invention. As used herein, the "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the invention. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. Preferably, the protein analogs are relatively resistant to in vivo degradation, resulting in a more prolonged therapeutic effect upon administration. Assays for measuring functional activity include, but are not limited to, those described in the Examples below.

Administration

Compositions comprising genetically modified immunoresponsive cells of the invention (e.g., T cells, NK cells, CTL cells, or their progenitors) can be provided systemically or directly to a subject for the treatment of a neoplasia, pathogen infection, or infectious disease. In one embodiment, cells of the invention are directly injected into an organ of interest (e.g., an organ affected by a neoplasia). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NK cells, or CTL cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus). Usually, at least $1 \times 10^5$ cells will be administered, eventually reaching $1 \times 10^{10}$, or more. Genetically modified immunoresponsive cells of the invention can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL-6, and IL-11, as well as the other interleukins, the colony stimulating factors, such as G-, M- and GM-CSF, interferons, e.g. $\gamma$-interferon and erythropoietin.

Compositions of the invention include pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

Formulations

Compositions of the invention comprising genetically modified immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical faun can be brought about by the use of agents delaying absorption, for example, aluminum monostearate and gelatin. According to the present invention, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage fowl, e.g., liquid dosage form (e.g., whether the composition is to be formulated into a solution, a suspension, gel or another liquid fowl, such as a time release form or liquid-filled form).

Those skilled in the art will recognize that the components of the compositions should be selected to be chemically inert and will not affect the viability or efficacy of the genetically modified immunoresponsive cells as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of genetically modified immunoresponsive cells of the invention is the quantity of cells necessary to achieve an optimal effect. The quantity of cells to be administered will vary for the subject being treated. In a one embodiment, between $10^4$ to $10^{10}$, between $10^5$ to $10^9$, or between $10^6$ and $10^8$ genetically modified immunoresponsive cells of the invention are administered to a human subject. In preferred embodiments, at least about $1\times10^8$, $2\times10^8$, $3\times10^8$, $4\times10^8$, and $5\times10^8$ genetically modified immunoresponsive cells of the invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Methods of Treatment

Provided herein are methods for treating neoplasia in a subject. Also contemplated herein are methods for treating a pathogen infection or other infectious disease in a subject, such as an immunocompromised human subject. The methods comprise administering a T cell, NK cell, or CTL cell of the invention in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the antigen-binding fragment administered.

For adoptive immunotherapy using antigen-specific T cells, cell doses in the range of $10^9$ are typically infused. Upon administration of the genetically modified cells into the host and subsequent differentiation, T cells are induced that are specifically directed against the specific antigen. "Induction" of T cells can include inactivation of antigen-specific T cells such as by deletion or anergy. Inactivation is particularly useful to establish or reestablish tolerance such as in autoimmune disorders. The modified cells can be administered by any method known in the art including, but not limited to, intravenous, subcutaneous, intranodal, intratumoral, intrathecal, intrapleural, intraperitoneal and directly to the thymus.

Therapeutic Methods

The invention provides methods for increasing an immune response in a subject in need thereof. In one embodiment, the invention provides methods for treating or preventing a neoplasia in a subject. The invention provides therapies that are particularly useful for the treatment of subjects having prostate cancer, or metastatic prostate cancer that is not amenable to conventional therapeutic interventions. Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in this invention is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included (but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes. Another group have a genetic predisposition to neoplasia but have not yet evidenced clinical signs of neoplasia. For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

Human neoplasia subjects having any of the following neoplasias: glioblastoma, melanoma, neuroblastoma, adenocarcinoma, glioma, soft tissue sarcoma, and various carcinomas (including prostate and small cell lung cancer) are especially appropriate subjects. Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Accordingly, the invention provides a method of treating or preventing a neoplasia in a subject, the method comprising administering an effective amount of an immunoresponsive cell comprising a receptor that binds a tumor antigen and a vector encoding a co-stimulatory ligand. In one embodiment, the neoplasia is selected from the group consisting of prostate cancer, colon cancer, breast cancer, and glioblastoma. In another embodiment, the tumor antigen is prostate-specific membrane antigen, CD19, NY-ESO-1, WT-1 or hTERT.

In another approach, the invention provides a method of enforcing tolerance in a subject, the method comprising administering an effective amount of an immunoresponsive cell comprising a receptor that binds an antigen and a vector encoding a co-stimulatory ligand. In one embodiment, the method prevents or reduces an autoimmune disease or a disease associated with allogeneic transplantation.

As a consequence of constitutive surface expression of co-stimulatory ligands, adoptively transferred human T or NK cells are endowed with augmented proliferative, cytolytic, and survival capacities in an intrinsically poorly immunogenic tumor or immunodeficient environment devoid of co-stimulatory ligands. Furthermore, subsequent to their localization to tumor or viral infection and their proliferation, co-stimulatory ligand-expressing T cells turn the tumor or viral infection site into a highly conductive environment for a wide range of immune cells involved in the physiological anti-tumor or antiviral response (tumor infiltrating lymphocytes, NK-, NKT-cells, dendritic cells, and macrophages).

In other embodiments, the invention provides methods for treating subjects with a pathogen infection (e.g., viral infection, bacterial infection, fungal infection, parasite infection, or protozoal infection. The invention is particularly useful for enhancing an immune response in an immunocompromised subject. Exemplary viral infections susceptible to treatment using a method of the invention include, but are not limited to, Cytomegalovirus (CMV), Epstein Ban Virus (EBV), Human Immunodeficiency Virus (HIV), and influenza virus infections.

Accordingly, the invention provides a method of treating or preventing a pathogen infection in a subject, the method comprising administering an effective amount of an immunoresponsive cell as described herein.

Kits

The invention provides kits for the treatment or prevention of a neoplasia, pathogen infection, immune disorder or allogeneic transplant. In one embodiment, the kit includes a therapeutic or prophylactic composition containing an effective amount of an immunoresponsive cell comprising one or more co-stimulatory ligands in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired the immunoresponsive cell is provided together with instructions for administering the cell to a subject having or at risk of developing a neoplasia, pathogen infection, immune disorder or allogeneic transplant. The instructions will generally include information about the use of the composition for the treatment or prevention of neoplasia, pathogen infection, immune disorder or allogeneic transplant. In other embodiments, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. Recombinant methods are well known in the art. The practice of the invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (Gait, ed., 1984); "Animal Cell Culture" (Freshney, ed., 1987); "Methods in Enzymology" (Academic Press, Inc.); "Handbook of Experimental Immunology" (Wei & Blackwell, eds.); "Gene Transfer Vectors for Mammalian Cells" (Miller & Calos, eds., 1987); "Current Protocols in Molecular Biology" (Ausubel et al., eds., 1987); "PCR: The Polymerase Chain Reaction", (Mullis et al., eds., 1994); and "Current Protocols in Immunology" (Coligan et al., eds., 1991). These techniques are applicable to the production of the polynucleotides and polypeptides, and, as such, can be considered in making and practicing the invention. Particularly useful techniques for are discussed in the sections that follow.

EXAMPLES

The following examples are provided as a further description of the invention, and to illustrate but not limit the invention.

Example 1

Figure 1C:
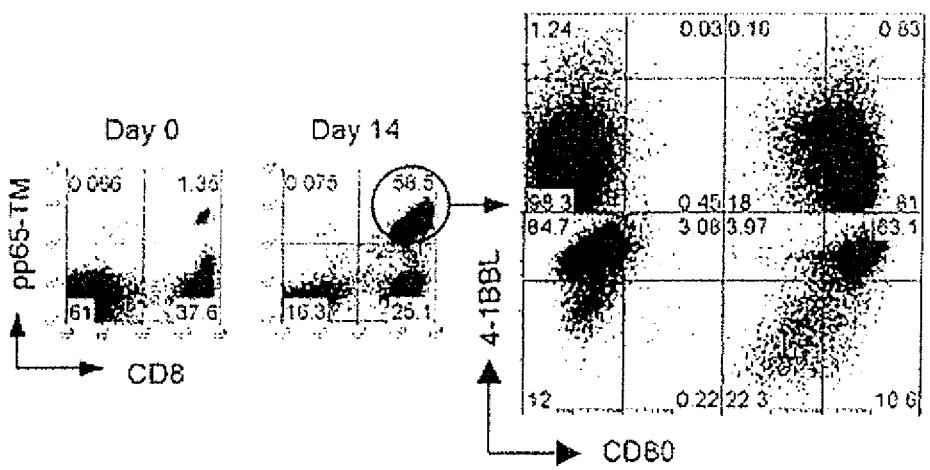

T Cells Co-Expressing CD80 and 4-1BBL Elicit Robust Proliferative Responses after Cyclic Stimulations through their Endogenous T Cell Receptor or Through a Chimeric Antigen Receptor without Antigen Presenting Cell (APC)-Provided Costimulation To assess whether constitutive expression of costimulatory ligands in T cells could substitute for APC-mediated costimulation, the T cell responses of human primary T cells were first investigated in three experimental systems. Using anti-CD3 (OKT3)-mediated T cell activation, the expansion of peripheral blood T lymphocytes transduced with CD80 and 4-1BBL was quantified (FIG. 1a), which were compared to T cells transduced with either ligand alone or none. Recurrent T cell receptor (TCR)-stimulation alone in the absence of costimulatory ligands failed to expand T cells and rapidly induced a decline in T cell number following the first restimulation (FIG. 1b). In sharp contrast, OKT3-stimulated $CD80^+$ $4-1BBL^+$ T cells triggered a mean 237-fold greater proliferation over 21 days. In comparison, T cells transduced with either ligand alone exhibited a mean 8.1-fold reduced proliferation ($p<0.0001$). Based on these observations, the concept of T-cell mediated costimulation was extended to two clinically relevant applications of adoptive T cell therapy, using cytomegalovirus (CMV)-specific memory donor T cells and differentiation antigen-specific, genetically redirected autologous T cells. CMV pp65-specific T lymphocytes briefly expanded on HLA-A*$0201^+$pp$65^+$ artificial APCs[24] were readily transduced with CD80 and 4-1BBL (FIG. 1c). Following exposure to the HLA-A*$0201^+$ pp65-transduced colonic tumor cell line Caco-2, T cells equipped with the costimulatory ligand pair CD80 and 4-1BBL exhibited a significantly greater (209-fold, $p<0.0001$) expansion, compared to a continuously declining T cell number in the control groups (FIG. 1d).

Figure 1E:
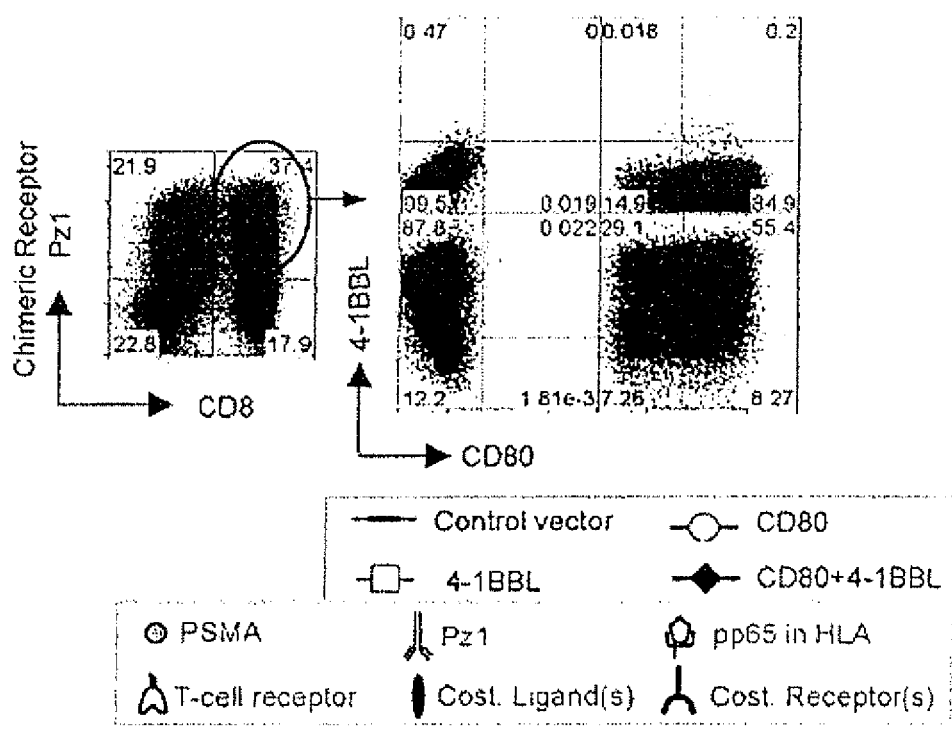

To rapidly generate tumor-reactive human T lymphocytes, peripheral blood T cells were retrovirally transduced with the chimeric antigen receptor Pz1 (Gade et al., Cancer Res. 65:9080-9088, 2005), a non-HLA-restricted antigen receptor specific for the tumor antigen PSMA. The Pz1 receptor comprises a PSMA-binding single chain antibody fragment fused to the human CD3 .zeta. signaling domain and is analogous in structure to other chimeric antigen receptors currently in use in clinical trials. $Pz1^+$ T cells coexpressing CD80 and 4-1BBL (FIG. 1e) mounted a robust proliferative response following three weekly stimulations with PSMA$^+$, CD80$^-$, CD86$^-$, 4-1BBL$^-$LNCaP cells (mean 1042-fold enrichment, FIG. 1f, upper panel). This expansion was 9-fold, greater ($p<0.0001$) than that obtained when expressing CD80 and 4-1BBL in the tumor cells rather than in the T cells (FIG. 1f, lower panel). Further analyses documented the greater induction of IL-2 and IFN-γ by exposure to PSMA in T cells coexpressing CD80 and 4-1BBL, as well as their greater antigen-specific cytolytic potential and decreased susceptibility to apoptosis, when compared to conventionally stimulated T lymphocytes (data not shown). In parallel studies, other members of TNF ligand family[5], including OX40L, CD27L (CD70) or CD30L, with or without CD80, were investigated and the combination of CD80 and 4-1BBL was found to be the most potent (data not shown).

In aggregate, these in vitro studies demonstrate the ability of T lymphocytes coexpressing CD80 and 4-1BBL cells to strongly potentiate suboptimal TCR-activation and, furthermore, to substitute for the lack of costimulation provided by the APC.

Example 2

T Cells Co-Expressing CD80 and 4-1BBL Eradicate Established, Systemic Tumors

To investigate the potency of our $CD80^+4$-$1BBL^+$ T cells in vivo, a model of multifocal, established prostate cancer utilizing $PSMA^+$ PC-3 tumor cells (Gong et al., Neoplasia 1:123-7, 1999, which is hereby incorporated by reference in its entirety) was developed. Using dual-modality bioluminescence and magnetic resonance imaging, tumors were visualized four weeks after intravenous inoculation, prior to initiating adoptive T cell therapy. The lungs, cervical lymph nodes, bone marrow, and liver were identified as the main sites of disease (FIG. 2a). In this model, animals were treated four weeks after tumor inoculation with a single intravenous infusion of $8 \times 10^6$ PSMA-targeted T cells, expressing either CD80, 4-1BBL, both, or neither.

In control mice treated with $8 \times 10^6$ CD19-targeted T cells, which, like untransduced T cells, fail to lyse $PSMA^+$ tumor targets in vitro tumor burden steadily progressed until mice had to be sacrificed (FIG. 2b,c). Treatment with $Pz1^+$T cells resulted in a short-term reduction of tumor burden, followed by terminal tumor progression (FIG. 2b), yielding a modest 12-day survival advantage (p=0.0001, FIG. 2c). Constitutive expression of either CD80 or 4-1BBL alone in PSMA-targeted T cells only marginally augmented this therapeutic response, extending the median survival to 63 and 66 days, respectively (p=0.077, p=0.056, respectively). T cells coexpressing CD80 and 4-1BBL induced major responses and reduced the tumor burden 3.3-fold (p=0.0028) four days after adoptive T cell transfer. A 1375-fold reduction was obtained after sixteen days, relative to the $Pz1^+$ T cell treatment group (p=0.0002). Seven of ten treated animals remained tumor-free 200 days after infusion of $Pz1^+CD80^+$ $4$-$1BBL^+$ T lymphocytes, and none in all other treatment or control groups (FIG. 2c). The three mice that failed therapy initially showed marked tumor regression before relapsing (FIG. 2b) and survived for 100 days (FIG. 2c).

Example 3

In Vivo T Cell Expansion Is Robust and Antigen-Specific

To track and quantify in vivo T-cell migration and accumulation in relation to tumor localization and tumor burden, adoptively transferred T cells were additionally marked with Click Beetle Red-luciferase (Ponomarev et al., Eur J Nucl Med Mol Imaging. 2004 May; 31(5):740-51) (CBR-luc, FIG. 3a). Serial imaging of mice treated with $Pz1^+$T cells showed a progressive increase in signal that reached a peak four days after T cell injection (FIG. 3b). A low-level signal remained detectable up to day 18. In the case of $Pz1^+CD80^+$ $4$-$1BBL^+$ T cells, peak signal was detected on day 8 (41-fold higher nadir photon count than $Pz1^+$ T cells, p=0.0009), which was followed by a gradual signal decline, although bioluminescence could still be detected until day 100 in some animals (FIG. 3b). Importantly, the effect of CD80 and 4-1BBL co-expression was abrogated in $19z1^+$T lymphocytes (FIG. 3b), consistent with the need for antigen stimulation for expansion to occur. Flow cytometric analyses and T cell counts of lung single cell suspensions in three treated mice per group determined the actual T cell number to be highly concordant with acquired bioluminescent signal intensities (FIG. 3c,d). These studies, therefore, demonstrate that T cells coexpressing CD80 and 4-1BBL expand in an antigen-dependent manner before eventually entering a contraction phase resulting in substantial, if not complete, T cell clearance.

Example 4

Figure 4B:
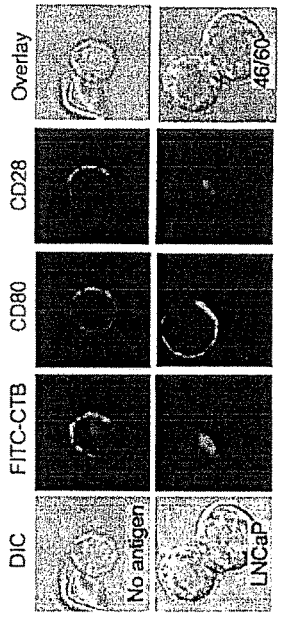
FIGS. 4a-4f show costimulation of T cells in cis as a result of the colocalization of CD80, 4-1BBL and their receptors CD28 and 4-1BB into the immunological synapse after induced T-cell/tumor cell cluster formation.
Figure 4D:
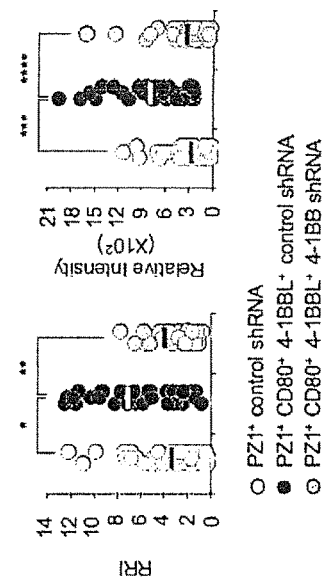
Figure 4F:
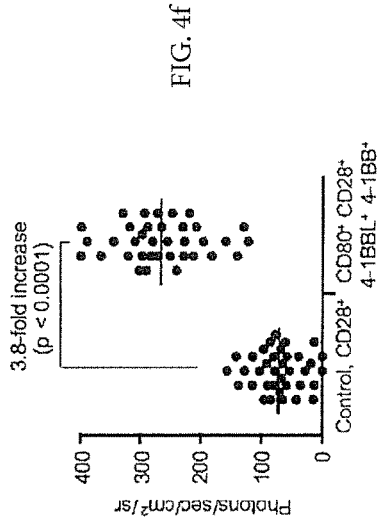
Figure 4A:
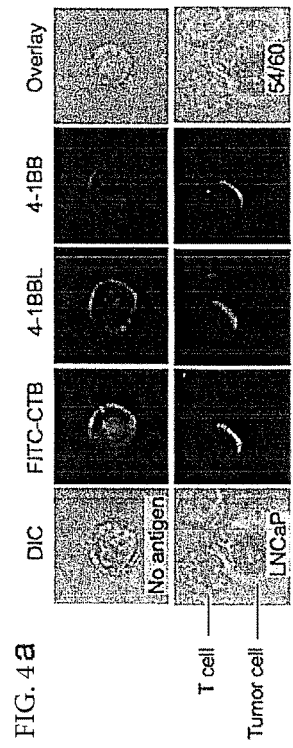
Figure 4C:
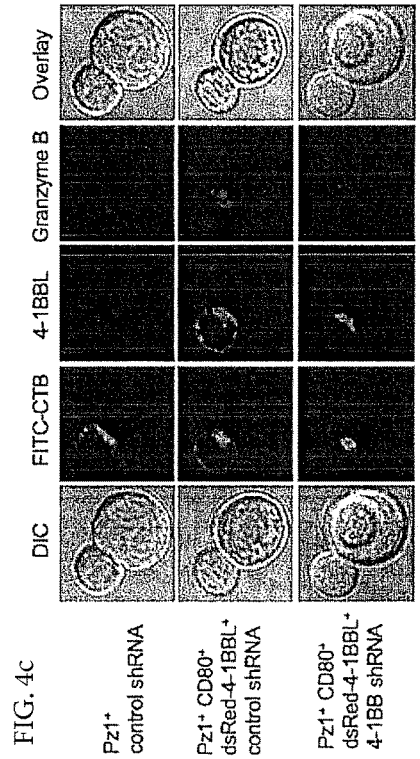

Coalescence of the Costimulatory Ligands CD80 and 4-1BBL with their Respective Receptors CD28 and 4-1BB in the Immunological Synapse Precedes Functional T Cell Auto-Costimulation To address whether constitutively expressed costimulatory ligands activate T cells in cis, the question of whether these ligands colocalize with their cognate receptors during T-cell activation was first examined. Both CD28 and 4-1BB amplify T cell receptor (TCR) signaling after recruitment into central membrane compartments of the immunological synapse[31-33]. Therefore, colocalization of CD80 and 4-1BBL to the T-cell tumor cell contact area is likely a prerequisite for auto-costimulation. To visualize 4-1BBL distribution by confocal microscopy, the cytoplasmic domain was fused to monomeric dsRed and this protein was coexpressed with CD80 in Pz1-transduced $CD8^+$ T lymphocytes. Immediately prior to admixing with unmodified $CD28^-$, $4$-$1BB^-$ LNCaP cells, T cells were labeled with fluorescein isothiocyanate-conjugated cholera toxin β subunit (FITC-CTB) to visualize lipid raft clusters after synapse formation. Following LNCaP tumor engagement, 4-1BBL and CD80, as well as 4-1BB and CD28, mobilized into choleratoxin-FITC-positive T-cell-tumor cell contact areas (FIG. 4a,b). To investigate the functional consequence of this interaction, the colocalization of Granzyme B (GRB. Defined, albeit sparse, GRB condensation was localized near the contact zone in clusters of Pz1-expressing $CD8^+$ T cells and their cognate tumor targets (FIG. 4c,d)) was examined and quantified. The median GRB recruitment to T-cell tumor cell junctions was amplified 2.2-fold in $CD80^+4$-$1BBL^+$ T cells (p=0.0001). To confirm that these observed differences were indeed a result of 4-1BB engagement with 4-1BBL within the same cell, 4-1BB expression was knocked down by stable coexpression of 4-1BBL and 4-1BB-specific shRNA (data not shown). Knock-down of 4-1BB significantly diminished GRB density near the synapse (2.02-fold reduction, p<0.0001), despite the presence of 4-1BBL at the T-cell junction in all imaged cell clusters. These findings strongly suggest that the costimulatory ligand functionally engages its receptor on the same T-cell surface after antigen-induced coalescence in the immunological synapse.

Figure 4E:
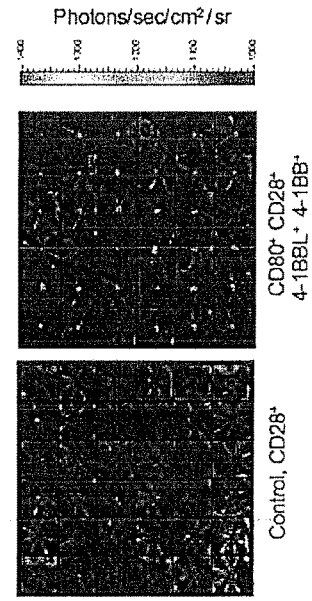

To further demonstrate auto-costimulation, a single cell assay was devised in which the endogenous 4-1BB/4-1BBL interaction could be analyzed following the earliest expression of 4-1BBL in recently transduced T cells. To achieve this, firefly luciferase was first expressed under the transcriptional control of NF-κB, a key downstream effector of 4-1BB signaling, in a clone of CD3$^+$CD28$^+$4-1BB$^-$ Jurkat T cells (JNL). To preclude NF-κB induction by sporadic bystander costimulation, JNL cells were exposed to retroviral vectors encoding 4-1BB, 4-1BBL and CD80, and subcloned by limiting dilution 4 hours thereafter, well before the first detectable surface gene expression (data not shown), and immediately stimulated by plate-bound OKT3. As illustrated in FIG. 4e, isolated CD80$^+$CD28$^+$4-1BBL$^+$4-1BB$^+$ T cells markedly up-regulated NF-κB, in contrast to JNL cells transduced with control vector. The luminescence signal was acquired in 36 wells containing a single, multiply transduced cell as described in Methods. Coexpression of the two ligand pairs increased NF-KB-dependent signal 3.8-fold (relative to control JNL; p<0.0001; FIG. 4f). Since at any point of this assay the sole source of costimulatory ligands was the isolated T cell's own surface, this NF-KB upregulation could only reflect the impact of auto-costimulation.

Example 5

In vitro Trans-Costimulation of Antigen-Specific Bystander T Cells

Figure 5A:
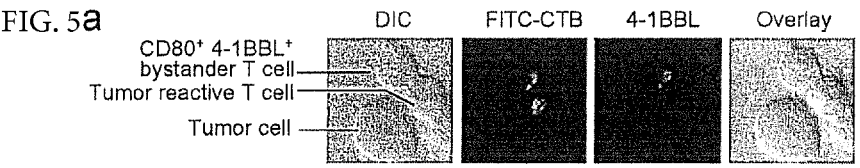
FIGS. 5a-5e show that CD80 and 4-1BBL-displaying T lymphocytes trans-costimulate unmodified, antigen specific bystander T-cells through physical contact.
Figure 5B:
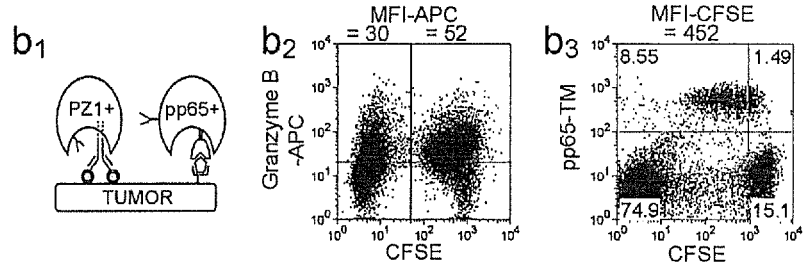
Figure 5C:
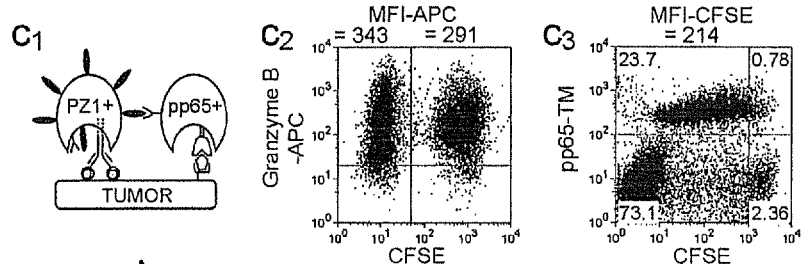
Figure 5D:
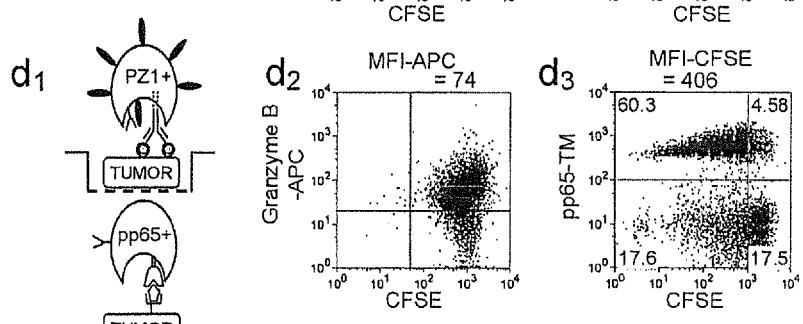
Figure 5E:
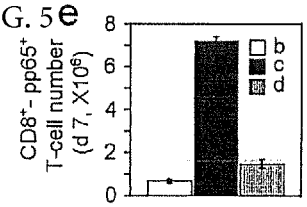

The constitutive expression of costimulatory ligands may also enable genetically modified T cells to costimulate T cells in trans. Notably, three-cell clusters comprised of CD80$^+$4-1BBL$^+$ and CD80$^-$ 4-1BBL$^-$ T cells were occasionally noted in the confocal studies shown in FIG. 4 (FIG. 5a). To provide functional evidence for trans-costimulation, a coculture system was devised in which PSMA-specific T cells expressing CD80 and 4-1BBL were admixed with carboxyfluoroscein succinimidyl ester (CFSE)-labeled T cells that were not transduced with CD80 or 4-1BBL. It was found that these CFSE-labeled, CMV pp65-specific T cells were effectively costimulated by autologous, bystander Pz1$^+$ CD80$^+$4-1BBL$^+$ T lymphocytes (FIG. 5b,c). Physical contact between the two T cell populations was a prerequisite for the CMV-reactive cytotoxic T lymphocytes to expand, as their separation by a transwell membrane greatly reduced the strong induction of GRB and the robust T-cell expansion mounted in pp65 responder cells, consistent with a cell contact-dependent mechanism (FIG. 5d).

Example 6

In Vivo Trans-Costimulation of Tumor-Infiltrating T Cells

Figures 6A, 6B:
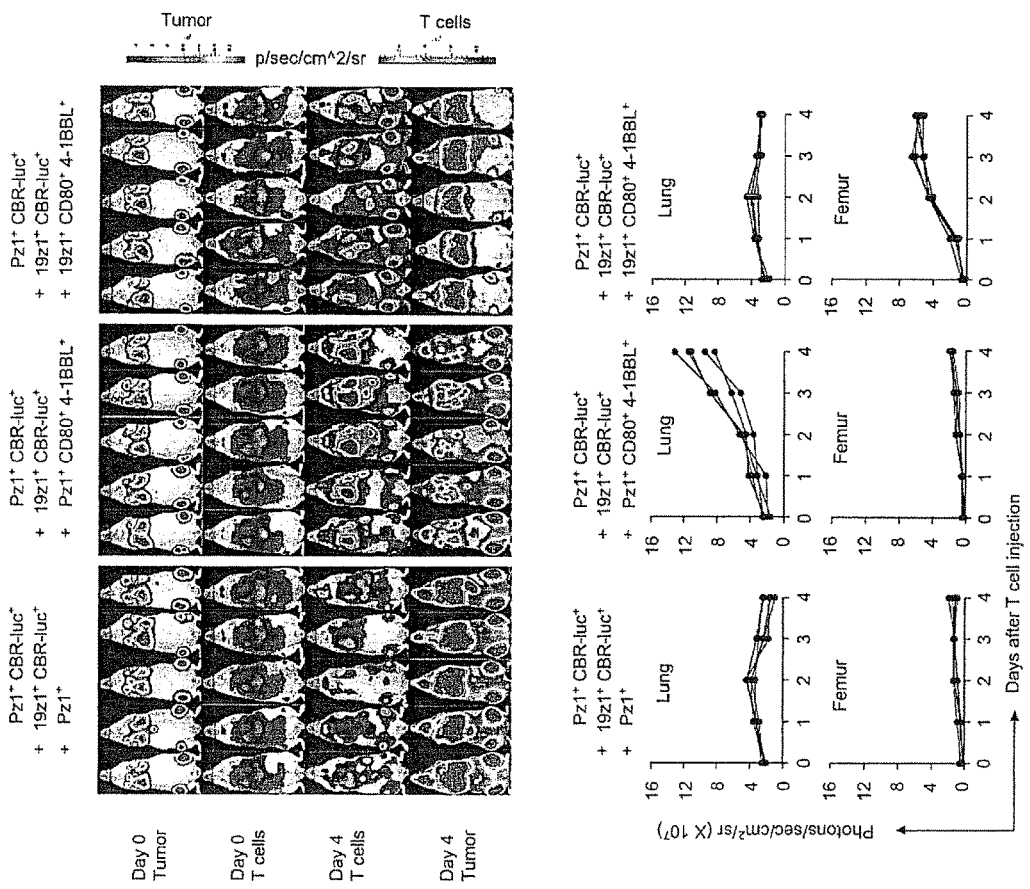
FIGS. 6a and 6b show that the accumulation of adoptively transferred PSMA-redirected T lymphocytes at tumor sites is augmented by Pz1$^+$CD80$^+$4-1BBL$^+$, but not 19z$^+$CD80$^+$4-1BBL$^+$ T-cells in Scid/beige mice.

These observations prompted us to investigate whether T cell-mediated trans-costimulation is operative in vivo. To this end, two previously described animal models were combined: the RM1-PSMA tumor model in which tumors are confined to the lungs (Gade et al., Cancer Res. 65:9080-9088, 2005), and the Raji tumor model, in which tumor cells selectively colonize bone marrow (Brentjens et al., Nat Med. 2003 March; 9(3):279-86). All mice were treated with Pz1-transduced T cells, which also expressed CBR-luc (FIG. 3). Luciferase-negative Pz1$^+$T cells, either expressing or lacking CD80 and 4-1BBL, were subsequently infused into the animals. The expression of Gaussia-luciferase (Gau-Luc) in the tumor cells, and of CBR-luc in Pz1+ T cells, allowed the use of dual bioluminescence imaging to simultaneously monitor tumor progression and the spatial and temporal accumulation of T cells. Comparable tissue distributions and bioluminescent signals of CBR-luc$^+$ lymphocytes were observed six hours (day 0) after adoptive transfer in all treatment groups (FIG. 6a). On day 2, the effect of Pz1$^+$CD80$^+$4-1BBL$^+$ T cells on CBR-luc$^+$Pz1$^+$ T cells was still modest (median 1.2-fold, relative to Pz1$^+$T cells as bystander, p=0.0947). The CBR-luc signal subsequently decayed in mice given control Pz1$^+$ T cells (FIG. 6a). In contrast, this photon count recorded over the thoracic area augmented 6.5-fold on average in mice given Pz1$^+$CD80$^+$ 4-1BBL$^+$ T lymphocytes (p=0.0122, FIG. 6a,b). Importantly, this effect was selective for the PSMA-targeted T cells, since co-injected CBR-luc$^+$ 19z1-transduced T cells, which infiltrated the established Raji tumors in both femurs, did not significantly enhance thoracic bioluminescent signal at any time point (median 1.5-fold increase on day 4, p=0.0947, FIG. 6a,b). Collectively, these in vitro and in vivo data indicate that CD80$^+$4-1BBC T cells locally enhance T-cell responses by providing costimulation in trans.

Figure 7:
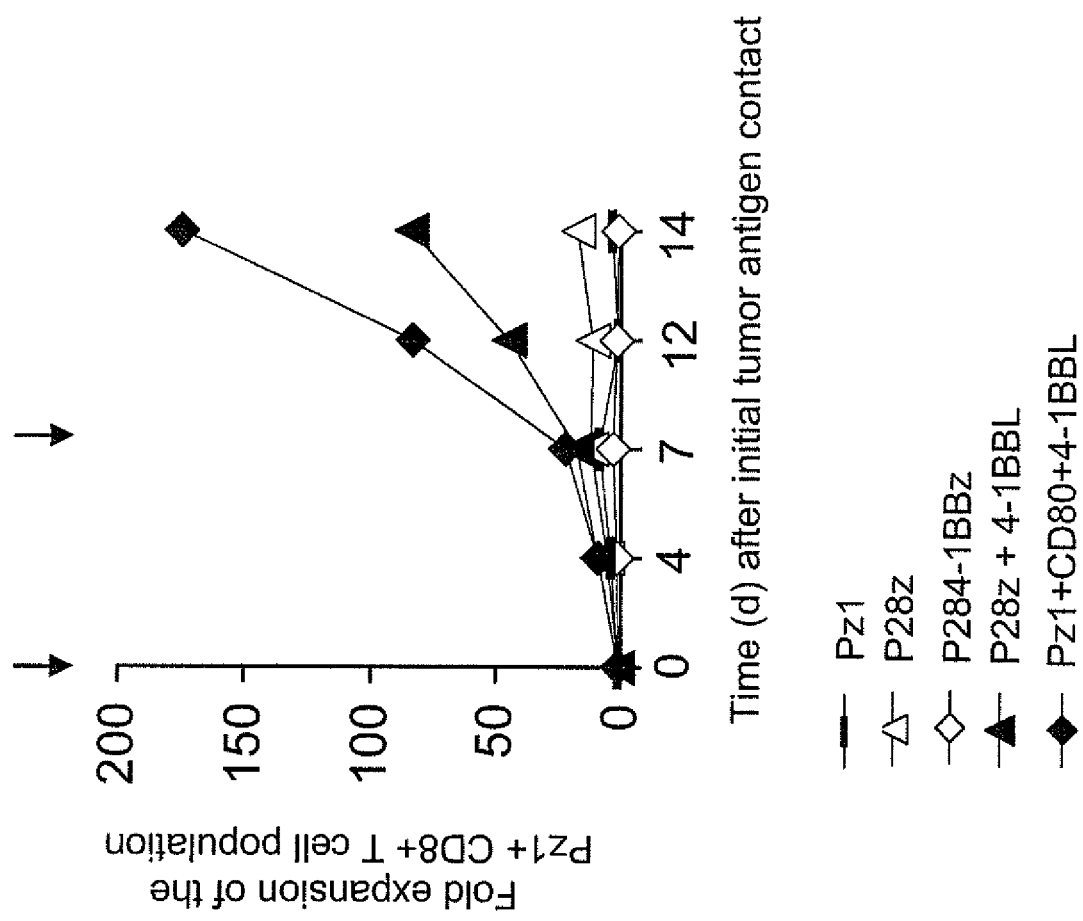
FIG. 7 shows that dual T cell-expressed CD80 and 4-1BBL elicits superior T cell expansion compared to CD28 and/or 4-1BB signaling elements fused in series with the Pz1 chimeric antigen receptor .zeta. signaling domain. Primary T cells were transduced with Pz1, P28z (Maher et al. Nature Biotechnology, Vol 20, January 2002, 70-75), which contains the CD28 signaling domain in series with the α chain, or P284-1BBz which includes both, CD28 and 4-1BB signaling regions. Alternatively, T lymphocytes were co-transduced with P28z and 4-1BBL (noted P28Z+4-1BBL). Pz1+CD80+4-1BBL refers to Pz1+ T cells that co-express both ligands, CD80 and 4-1BBL. Transduced T cells were stimulated weekly (indicated by arrows) on LNCaP tumor monolayers under conditions outlined in detail under FIG. 1. The fold expansion of the CD8$^+$ Pz1 -transduced human T lymphocytes population is graphed.
Figure 8:
FIG. 8 provides amino acid sequences for CD80, 4-1BBL, OX40L, CD70, LIGHT, and CD30 L.
Figure 8:

The constitutive display of CD80 on T lymphocytes serves as a costimulatory ligand for CD28 but could also engage negative regulators of T cell expansion, such as CTLA-4 at high affinities (Hodi et al. Clin Cancer Res. 2007 Sep. 15:13:5238-42). To bypass therapeutically undesirable T cell auto-inhibition mediated by T cell-expressed CD80, T lymphocytes were co-transduced with the chimeric antigen receptor P28z (Maher et al. Nature Biotechnology, Vol 20, January 2002, P 70-75) and expressed 4-1BBL on the T cell surface (FIG. 7). The dual fusion receptor P28z contains both TCR and CD28 signaling moieties. Whereas signaling through P28z failed to invoke a sustained T cell expansion, the co-expression of 4-1BBL markedly enhanced the proliferative response more than 10-fold by day 14. The synergistic CD80-4-1BBL costimulatory signal, however, was still strongest when both full length ligands were expressed on the surface of Pz1-transduced T lymphocytes (approximately two-fold higher than P28Z+4-1BBL, FIG. 7). CD28 signals relayed by a CD28 signaling element fused into the chimeric antigen receptor construct can therefore endow Pz1$^+$4-1BBL$^+$T lymphocytes with enhanced proliferative properties, although it is not as robust a T cell proliferation than observed in Pz1$^+$4-1BBL$^+$CD80$^+$ T cells.

A major goal of cancer immunotherapy is to provide safe and effective costimulation to tumor-reactive T lymphocytes. Using a genetic approach, it was demonstrated that T cells themselves provide potent costimulation. Constitutive expression of costimulatory ligands in human primary CMV-specific cells and PSMA-targeted T cells not only compensated for the absence of these ligands on APCs, but also induced a proliferative response surpassing that elicited by conventional APCs (FIG. 1). The survey of a panel of costimulatory ligands indicated that CD80 and 4-1BBL provided the strongest T-cell activation under our experimental conditions, enabling robust T cell expansion following repeated weekly antigenic stimulation. CD80$^+$4-1BBL$^+$ T cells exhibited superior proliferation, cytokine secretion, in vitro survival and in vivo expansion and persistence, resulting in a 40- to 50-fold greater T cell biomass one week after infusion in tumor-bearing mice, when compared to PSMA-specific T cells that were not transduced with CD80 and 4-1BBL (FIG. 3). Whereas animals treated with non-CD80/4-1BBL-transduced PSMA-specific T cells uniformly succumbed to disease, infusion of the same T cells rendered CD80$^+$ 4-1BBL$^+$ effectively rejected established, systemic PC-3 tumors in the majority of treated mice (FIG. 2). These findings, obtained in a very challenging tumor model, underscore the biological activity and remarkable potency of constitutive, high-level expression of costimulatory ligands in T cells.

To investigate the mechanism underlying this potentiated response, the spatial distribution of CD80 and 4-1BBL and their receptors on T cells before and after tumor engagement were first examined. CD28 and 4-1BB have been shown to accumulate in close proximity to the TCR within the central supramolecular activation cluster of immunological synapses. Costimulatory ligands expressed by APCs, including CD80 CD40L and CD70, polarize to the synapse, supporting the notion that the immunological synapse provides an ordered contact area to facilitate and propagate costimulatory ligand-receptor interactions. Consistent with this model, T-cell-encoded CD80 and 4-1BBL polarized towards the contact zone between T cells and LNCaP tumor cells with, together with CD28 and 4-1BB (FIG. 4). The functional consequence of this colocalization is illustrated by the accumulation of GRB, which is ferried towards the T cell-APC interface along microtubules following antigen contact in synapses containing 4-1BB$^+$4-1BBL$^+$ foci but not in T cells lacking 4-1BB (FIG. 4). The immunological synapse is thus apparently well suited to orchestrate auto-costimulation.

Auto-costimulation was demonstrated in a single cell assay in which de novo expression of 4-1BB and 4-1BBL in recently transduced T cells activated NF-κB without any possible contribution from a neighboring T cell. NF-κB expression was visualized in real-time, after physical separation of single clones shortly after transduction, several hours before costimulatory ligand expression could be detected (FIG. 4). Auto-costimulation may thus allow T lymphocytes to override the poor costimulatory capacity of suboptimal APCs, including tumor cells. Furthermore, constitutive cell surface expression of 4-1BBL in T cells ensures costimulation 'on demand' by ensuring that the ligand remains ready to engage transiently upregulated receptors such as 4-1BB. One might speculate that the physical interaction of 4-1BBL with its receptor may occur during early raft reorganization or between opposing plasma membrane folds at the center of the synapse. This effect appears to be self-regulated as CD80$^+$4-1BBL$^+$ T-cell expansion was gradually attenuated in response to repeated in vitro antigen exposure (FIG. 1). In vivo T-cell expansion was also self-limited (FIG. 3), which may be due to tumor elimination that deprives the T cells of antigenic stimulation and attenuated costimulatory signaling.

Without wishing to be bound by theory, our studies also support trans-costimulation as a mechanism for enhancing immunity through high-level expression of CD80 and 4-1BBL in T lymphocytes. The proliferative and effector functions of T cells engaging APC-presented antigen in the absence of CD80 or 4-1BBL were thus amplified by in vitro coculture or in vivo coadministration of T cells displaying both ligands. In vitro cell mixing and transwell studies indicated that trans-costimulation required cell-cell contact (FIG. 5), in agreement with trans effects reported for other cell types such as fibroblasts or bystander tumor cells. Trans-costimulation was also induced in vivo, in organ-specific fashion, as illustrated in mice bearing two different tumors segregating to different sites (FIG. 6).

Trans-costimulation mediated by T cells paves the way for exciting new therapeutic approaches since costimulation may be delivered to neighboring T cells within the tumor microenvironment. This feature is especially valuable as dendritic cells frequently fail to fully upregulate costimulatory ligands within the tumor microenvironment. Although soluble factors such as interleukin-2 may contribute to T cell aid, the dependence on cell-cell contact effectively restricts trans-costimulation to other tumor-infiltrating T cells. Without wishing to be bound by theory, the effect of T cell competition on the in vivo frequency of trans-costimulation. in trans may ultimately broaden the anti-tumor immune response via the recruitment of a diverse population of endogenous tumor-infiltrating lymphocytes and thus help to prevent tumor antigen escape.

In summary, it was shown that CD80 and 4-1BBL expression in human T lymphocytes is a biologically efficacious means to circumvent the lack of conventional APC-mediated costimulation in the tumor microenvironment. This approach is applicable to T cells activated through a transduced antigen receptor as well as their endogenous TCR. T cell-mediated costimulation, whether in auto, trans or both, may thus be useful in a wide range of malignancies and infectious diseases that are being treated by adoptive T cell therapy.

EMBODIMENTS OF THE INVENTION

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

What is claimed is:

1. A method of treating leukemia or ovarian cancer in a subject, comprising administering an effective amount of immunoresponsive cells to the subject, wherein the immunoresponsive cell comprises:
   a) a chimeric antigen receptor (CAR) that binds to a tumor antigen expressed by leukemia or ovarian cancer, and
   b) a nucleic acid molecule encoding a recombinant IL-12.

2. The method of claim 1, wherein the cell is a T cell.

3. The method of claim 1, wherein the cell comprises a cytotoxic T lymphocyte.

4. The method of claim 1, wherein the nucleic acid molecule is comprised on a vector.

5. The method of claim 4, wherein the vector is a viral vector.

6. The method of claim 5, wherein the vector is a retroviral vector.

7. The method of claim 6, wherein the retroviral vector is a gamma-retroviral vector or a lentiviral vector.

8. The method of claim 1, wherein the tumor antigen is CD19.

9. The method of claim 1, wherein the tumor antigen is expressed by a tumor expressing CD19.

10. The method of claim 1, wherein the CAR comprises a ζ chain signaling domain.

11. The method of claim 1, wherein the CAR further comprises a domain that provides a costimulatory signal.

12. The method of claim 1, wherein the CAR comprises a CD28 signaling element.

13. The method of claim 1, wherein the immunoresponsive cell is a T cell, and the tumor antigen is expressed by ovarian cancer.

14. The method of claim 1, wherein the immunoresponsive cell is a T cell, and the tumor antigen is expressed by leukemia.

15. The method of claim 1, wherein the leukemia is acute lymphocytic leukemia.

* * * * *

SEQUENCE LISTING

<160> NUMBER OF SEQ ID NOS: 7

<210> SEQ ID NO 1
<211> LENGTH: 288
<212> TYPE: PRT
<213> ORGANISM: Homo sapiens

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

-continued

```
Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 2
<211> LENGTH: 254
<212> TYPE: PRT
<213> ORGANISM: Homo sapiens

<400> SEQUENCE: 2

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140
```

```
Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 3
<211> LENGTH: 67
<212> TYPE: PRT
<213> ORGANISM: Homo sapiens

<400> SEQUENCE: 3

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr
65

<210> SEQ ID NO 4
<211> LENGTH: 193
<212> TYPE: PRT
<213> ORGANISM: Homo sapiens

<400> SEQUENCE: 4

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140
```

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
            165                 170                 175

Pro Ser Arg Asn Thr Asp Glu Thr Phe Phe Gly Val Gln Trp Val Arg
            180                 185                 190

Pro

<210> SEQ ID NO 5
<211> LENGTH: 204
<212> TYPE: PRT
<213> ORGANISM: Homo sapiens

<400> SEQUENCE: 5

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Asp Gly Pro Ala Gly Ser Trp Glu Gln Leu Ile
        35                  40                  45

Gln Glu Arg Arg Ser His Glu Val Asn Pro Ala Ala His Leu Thr Gly
    50                  55                  60

Ala Asn Ser Ser Leu Thr Gly Ser Gly Gly Pro Leu Leu Trp Glu Thr
65                  70                  75                  80

Gln Leu Gly Leu Ala Phe Leu Arg Gly Leu Ser Tyr His Asp Gly Ala
                85                  90                  95

Leu Val Val Thr Lys Ala Gly Tyr Tyr Tyr Ile Tyr Ser Lys Val Gln
            100                 105                 110

Leu Gly Gly Val Gly Cys Pro Leu Gly Leu Ala Ser Thr Ile Thr His
        115                 120                 125

Gly Leu Tyr Lys Arg Thr Pro Arg Tyr Pro Glu Glu Leu Glu Leu Leu
    130                 135                 140

Val Ser Gln Gln Ser Pro Cys Gly Arg Ala Thr Ser Ser Ser Arg Val
145                 150                 155                 160

Trp Trp Asp Ser Ser Phe Leu Gly Gly Val Val His Leu Glu Ala Gly
                165                 170                 175

Glu Glu Val Val Val Arg Val Leu Asp Glu Arg Leu Val Arg Leu Arg
            180                 185                 190

Asp Gly Thr Arg Ser Tyr Phe Gly Ala Phe Met Val
        195                 200

<210> SEQ ID NO 6
<211> LENGTH: 234
<212> TYPE: PRT
<213> ORGANISM: Homo sapiens
<220> FEATURE:
<221> NAME/KEY: MOD_RES
<222> LOCATION: (160)..(160)
<223> OTHER INFORMATION: Any amino acid
<220> FEATURE:
<221> NAME/KEY: MOD_RES
<222> LOCATION: (172)..(172)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (230)..(230)

<223> OTHER INFORMATION: Any amino acid

<400> SEQUENCE: 6

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
                20                  25                  30

Thr Thr Ser Arg Ser Tyr Phe Tyr Leu Thr Thr Ala Thr Leu Ala Leu
            35                  40                  45

Cys Leu Val Phe Thr Val Ala Thr Ile Met Val Leu Val Val Gln Arg
50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
                100                 105                 110

Leu Ser Trp Asn Lys Asp Gly Ile Leu His Gly Val Arg Tyr Gln Asp
            115                 120                 125

Gly Asn Leu Val Ile Gln Phe Pro Gly Leu Tyr Phe Ile Ile Cys Gln
130                 135                 140

Leu Gln Phe Leu Val Gln Cys Pro Asn Asn Ser Val Asp Leu Lys Xaa
145                 150                 155                 160

Glu Leu Leu Ile Asn Lys His Ile Lys Lys Gln Xaa Leu Val Thr Val
                165                 170                 175

Cys Glu Ser Gly Met Gln Thr Lys His Val Tyr Gln Asn Leu Ser Gln
                180                 185                 190

Phe Leu Leu Asp Tyr Leu Gln Val Asn Thr Thr Ile Ser Val Asn Val
            195                 200                 205

Asp Thr Xaa Gln Tyr Ile Asp Thr Ser Thr Phe Pro Leu Glu Asn Val
        210                 215                 220

Leu Ser Ile Phe Leu Xaa Ser Asn Ser Asp
225                 230

<210> SEQ ID NO 7
<211> LENGTH: 329
<212> TYPE: PRT
<213> ORGANISM: Homo sapiens

<400> SEQUENCE: 7

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
                20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
                100                 105                 110

His His Lys Lys Pro Thr Gly Met Ile Arg Ile His Gln Met Asn Ser

-continued

```
            115                 120                 125
Glu Leu Ser Val Leu Ala Asn Phe Ser Gln Pro Glu Ile Val Pro Ile
        130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```